US012629147B2

(12) United States Patent
Bar-On et al.

(10) Patent No.: US 12,629,147 B2
(45) Date of Patent: May 19, 2026

(54) TISSUE MANIPULATION WITH AN ENDOLUMINAL GASTROPLASTY DEVICE

(71) Applicant: Nitinotes Ltd., Caesarea (IL)

(72) Inventors: Raz Bar-On, Hadera (IL); Gilad Heftman, Pardes Hana Karkur (IL); Itshak Cohen, Ramat-HaSharon (IL); Eli Shapira, Kfar Saba (IL); Marina Dror, Haifa (IL)

(73) Assignee: Nitinotes Ltd., Caesarea (IL)

( * ) Notice: Subject to any disclaimer, the term of this patent is extended or adjusted under 35 U.S.C. 154(b) by 897 days.

(21) Appl. No.: 17/421,444

(22) PCT Filed: Jan. 9, 2020

(86) PCT No.: PCT/IL2020/050041
§ 371 (c)(1),
(2) Date: Jul. 8, 2021

(87) PCT Pub. No.: WO2020/144693
PCT Pub. Date: Jul. 16, 2020

(65) Prior Publication Data
US 2022/0079577 A1 Mar. 17, 2022

Related U.S. Application Data

(60) Provisional application No. 62/790,070, filed on Jan. 9, 2019.

(51) Int. Cl.
*A61B 17/062* (2006.01)
*A61B 17/00* (2006.01)
(Continued)

(52) U.S. Cl.
CPC ........ *A61B 17/062* (2013.01); *A61B 17/0487* (2013.01); *A61B 2017/00818* (2013.01);
(Continued)

(58) Field of Classification Search
CPC ............... A61B 17/06; A61B 17/0487; A61B 17/06066; A61B 17/0469;
(Continued)

(56) References Cited

U.S. PATENT DOCUMENTS 3,732,858 A * 5/1973 Banko .............. A61B 17/32002
606/107
4,935,025 A * 6/1990 Bundy ................... A61B 10/04
600/564

(Continued)

FOREIGN PATENT DOCUMENTS

CN 1822794 8/2006
CN 101044996 10/2007
(Continued)

OTHER PUBLICATIONS

Machine Translation Dated Jul. 30, 2024 of Notification of Office Action and Search Report Dated Jul. 22, 2024 From the National Intellectual Property Administration of the People's Republic of China Re. Application No. 202080019590.6. (11 Pages).
(Continued)

*Primary Examiner* — Tan-Uyen T Ho
*Assistant Examiner* — Osama Nemer

(57) ABSTRACT

Devices and methods of endolumenal formation of gastric sleeves are described. In some embodiments, a bougie capsule section comprises one or more mechanisms to allow flexing that induces a bend through a suction clamping domain that grabs, positions, and holds body lumen tissue (e.g., gastric wall tissue). In some embodiments, a needle drive is configured to allow longitudinal movement of a helical needle through a suturing space defined by the suction clamping domain, optionally while the suction clamping domain is bent. In some embodiments, the suction clamping domain can insert to the stomach in a collapsed configuration, then expanded once in the stomach. Poten-
(Continued)

Figure 1:
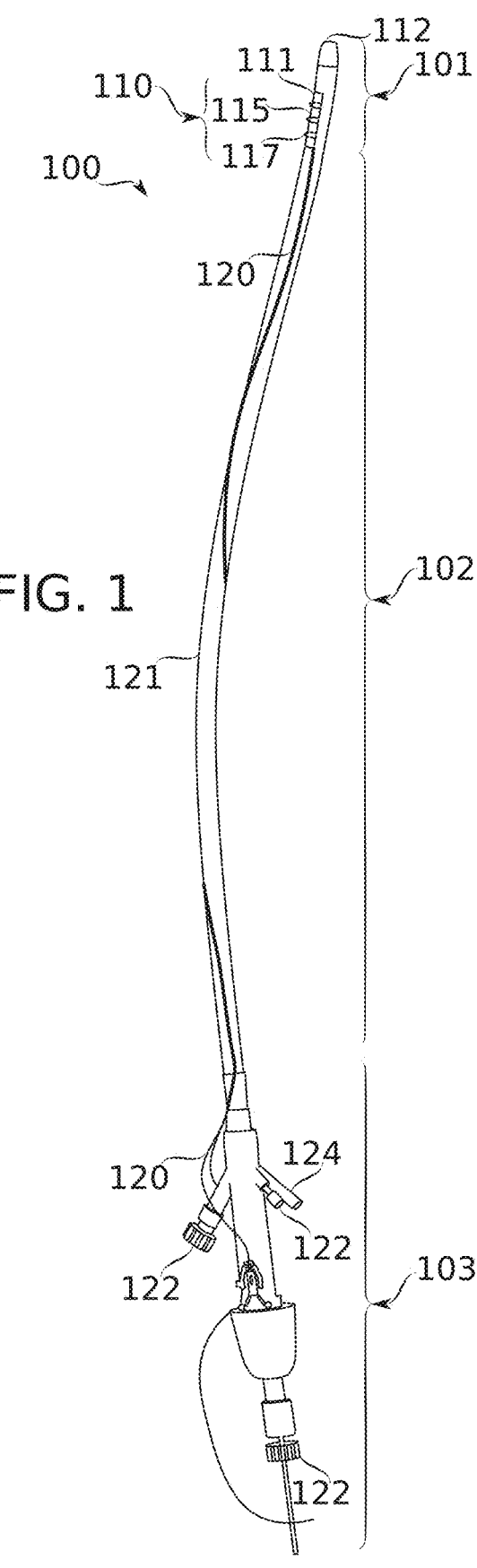

tially, this allows grabbing and positioning larger and/or deeper folds of tissue for suturing.

29 Claims, 18 Drawing Sheets

(51) Int. Cl.
  *A61B 17/04*          (2006.01)
  *A61B 17/06*          (2006.01)
(52) U.S. Cl.
  CPC ............... *A61B 2017/06076* (2013.01); *A61B 2217/005* (2013.01)
(58) Field of Classification Search
  CPC ........... A61B 2017/00818; A61B 2017/06076; A61B 2017/306; A61B 2217/005; A61B 1/00; A61B 17/00; A61B 17/062; A61B 90/00; A61F 5/0083; B32B 27/00
  See application file for complete search history.

(56)                    References Cited

U.S. PATENT DOCUMENTS

| | | | |
|---|---|---|---|
| 5,545,148 A | 8/1996 | Wurster | |
| 5,947,983 A * | 9/1999 | Solar | A61B 17/0469 606/144 |
| 6,400,979 B1 * | 6/2002 | Stoianovici | A61B 90/36 600/429 |
| 6,558,400 B2 | 5/2003 | Deem et al. | |
| 6,986,776 B2 * | 1/2006 | Craig | A61B 17/0625 606/139 |
| 7,083,629 B2 | 8/2006 | Weller et al. | |
| 7,758,493 B2 * | 7/2010 | Gingras | A61F 5/0086 600/37 |
| 7,766,925 B2 | 8/2010 | Stokes et al. | |
| 7,779,845 B2 | 8/2010 | Ortiz | |
| 7,896,890 B2 | 3/2011 | Ortiz et al. | |
| 8,075,573 B2 | 12/2011 | Gambale et al. | |
| 8,454,683 B2 * | 6/2013 | Rafiee | A61F 2/2451 623/2.11 |
| 8,500,757 B2 * | 8/2013 | Miraki | A61B 17/0482 606/139 |
| 8,906,039 B2 | 12/2014 | Crainich | |
| 8,906,040 B2 | 12/2014 | Filipi et al. | |
| 8,939,902 B2 | 1/2015 | Roth et al. | |
| 8,992,570 B2 | 3/2015 | Gambale et al. | |
| 9,149,270 B2 | 10/2015 | Fogel | |
| 9,277,915 B2 * | 3/2016 | Belson | A61B 17/3421 |
| 9,649,114 B2 * | 5/2017 | Viker | A61B 17/3468 |
| 9,730,687 B2 * | 8/2017 | Shluzas | A61B 17/0469 |
| 10,149,677 B2 * | 12/2018 | Belson | A61B 17/0482 |
| 11,357,549 B2 * | 6/2022 | Kiester | A61B 17/7023 |
| 11,690,745 B2 * | 7/2023 | Keren | A61F 5/0083 606/144 |
| 12,042,141 B2 * | 7/2024 | Smith | A61B 17/06066 |
| 2002/0107530 A1 | 8/2002 | Sauer et al. | |
| 2002/0183768 A1 * | 12/2002 | Deem | A61B 17/1114 606/151 |
| 2003/0171760 A1 | 9/2003 | Gambale | |
| 2004/0158125 A1 | 8/2004 | Aznoian | |
| 2006/0212048 A1 * | 9/2006 | Crainich | A61B 17/0469 606/144 |
| 2006/0253126 A1 | 11/2006 | Bjerken et al. | |
| 2006/0253127 A1 * | 11/2006 | Bjerken | A61B 17/0482 606/139 |
| 2006/0282094 A1 | 12/2006 | Stokes | |
| 2007/0055292 A1 | 3/2007 | Ortiz et al. | |
| 2007/0129735 A1 | 6/2007 | Filipi et al. | |
| 2008/0249404 A1 | 10/2008 | Mikkaichi et al. | |
| 2008/0275473 A1 | 11/2008 | Filipi | |
| 2009/0105816 A1 * | 4/2009 | Olsen | A61F 2/2466 623/2.37 |
| 2012/0022560 A1 | 1/2012 | Ferreira | |
| 2012/0165750 A1 * | 6/2012 | Plumptre | A61M 5/31585 604/207 |
| 2012/0172809 A1 * | 7/2012 | Plumptre | A61M 5/31525 604/207 |
| 2012/0204865 A1 | 8/2012 | Filipi et al. | |
| 2014/0155915 A1 | 6/2014 | Mikkaichi et al. | |
| 2016/0250056 A1 * | 9/2016 | Keren | A61B 17/0491 606/144 |
| 2017/0304099 A1 * | 10/2017 | Keren | A61B 17/072 |
| 2020/0030130 A1 * | 1/2020 | Keren | A61B 17/0469 |
| 2022/0000473 A1 * | 1/2022 | Mann | A61B 17/0469 |
| 2022/0079577 A1 * | 3/2022 | Bar-On | A61F 5/0083 |
| 2022/0233189 A1 | 7/2022 | Azar et al. | |
| 2023/0355232 A1 * | 11/2023 | Asherov | A61B 17/0625 |

FOREIGN PATENT DOCUMENTS

| | | | | |
|---|---|---|---|---|
| CN | 101209214 | 7/2008 | | |
| CN | 102405022 | 4/2012 | | |
| CN | 106999177 | 8/2017 | | |
| EP | 2861159 | 2/2018 | | |
| EP | 3052176 B1 * | 5/2019 | ........ | A61M 25/0606 |
| EP | 3476325 | 5/2019 | | |
| EP | 2785497 | 10/2022 | | |
| JP | 2004-500206 | 1/2004 | | |
| JP | 2004-514462 | 5/2004 | | |
| JP | 2005-161050 | 6/2005 | | |
| JP | 2007-500575 | 1/2007 | | |
| JP | 2007-275577 | 10/2007 | | |
| JP | 2008-132328 | 6/2008 | | |
| JP | 2008-161686 | 7/2008 | | |
| JP | 2009-532074 | 9/2009 | | |
| JP | 2012-506756 | 3/2012 | | |
| JP | 2017-533791 | 11/2017 | | |
| KR | 10-1857507 | 5/2018 | | |
| WO | WO 01/66001 | 9/2001 | | |
| WO | WO 2004/103189 | 12/2004 | | |
| WO | WO 2007/098212 | 8/2007 | | |
| WO | WO 2008/069816 | 6/2008 | | |
| WO | WO 2009/084436 | 7/2009 | | |
| WO | WO-2009084436 A1 * | 7/2009 | ....... | A61B 17/06066 |
| WO | WO 2010/050910 | 5/2010 | | |
| WO | WO 2016/056016 | 4/2016 | | |
| WO | WO 2020/144693 | 7/2020 | | |
| WO | WO 2021/171290 | 9/2021 | | |

OTHER PUBLICATIONS

Notification of Office Action and Search Report Dated Jul. 22, 2024 From the National Intellectual Property Administration of the People's Republic of China Re. Application No. 202080019590.6. (11 Pages).

Notice of Reason(s) for Rejection Dated Mar. 12, 2024 From the Japan Patent Office Re. Application No. 2021-540026 and Its Translation Into English. (5 Pages).

Supplementary European Search Report and the European Search Opinion Dated Mar. 20, 2024 From the European Patent Office Re. Application No. 21760195.4. (9 Pages).

Notice of Reason(s) for Rejection Dated From the Japan Patent Office Re. Application No. 2021-540026 and Its Translation Into English. (21 Pages).

English Summary Dated Jan. 29, 2024 of Notification of Office Action Dated Jan. 11, 2024 From the National Intellectual Property Administration of the People's Republic of China Re. Application No. 202080019590.6 (2 Pages).

Notification of Office Action Dated Jan. 11, 2024 From the National Intellectual Property Administration of the People's Republic of China Re. Application No. 202080019590.6 and Its Machine Translation Into English. (9 Pages).

Supplementary European Search Report and the European Search Opinion Dated Sep. 21, 2022 From the European Patent Office Re. Application No. 20738264.9. (11 pages).

International Preliminary Report on Patentability Dated Jul. 22, 2021 From the International Bureau of WIPO Re. Application No. PCT/IL2020/050041. (10 Pages).

(56) References Cited

OTHER PUBLICATIONS

International Search Report and the Written Opinion Dated Apr. 2, 2020 From the International Searching Authority Re. Application No. PCT/IL2020/050041. (16 Pages).

International Search Report and the Written Opinion Dated May 27, 2021 From the International Searching Authority Re. Application No. PCT/IL2021/050208. (25 Pages).

Invitation to Pay Additional Fees and Communication Relating to the Results of the Partial International Search Dated May 2, 2021 From the International Searching Authority Re. Application No. PCT/IL2021/050208. (5 Pages).

Notification of Office Action and Search Report Dated Sep. 19, 2024 From the State Intellectual Property Office of the People's Republic of China Re. Application No. 202180027964.3 and Its Machine Translation and English Summary. (20 Pages).

English Summary Dated Aug. 6, 2024 of Notification of Office Action Dated Jul. 22, 2024 From the National Intellectual Property Administration of the People's Republic of China Re. Application No. 202080019590.6. (5 Pages).

Communication Pursuant to Article 94(3) EPC Dated Dec. 17, 2024 From the European Patent Office Re. Application No. 21760195.4. (3 Pages).

Notification of Office Action Dated Dec. 17, 2024 From the National Intellectual Property Administration of the People's Republic of China Re. Application No. 202080019590.6 and Its Machine Translation Into English. (9 Pages).

Notice of Reasons for Rejection Dated Oct. 22, 2024 From the Japan Patent Office Re. Application No. 2022-550975 and its Translation Into English. (11 Pages).

* cited by examiner

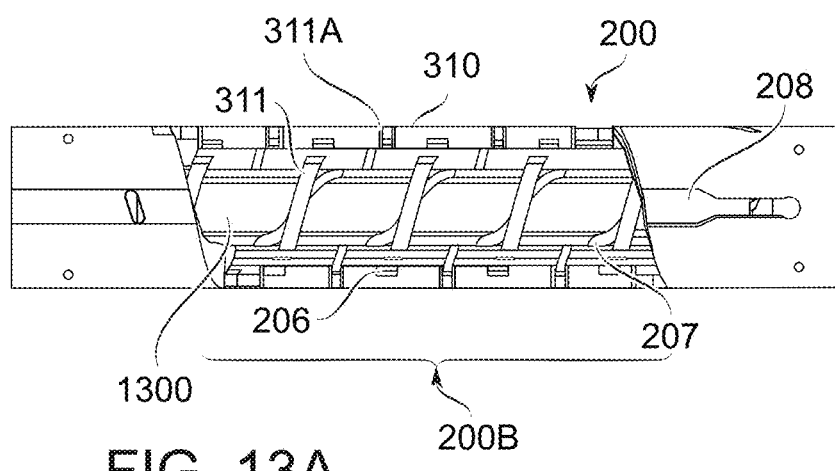
FIG. 13A
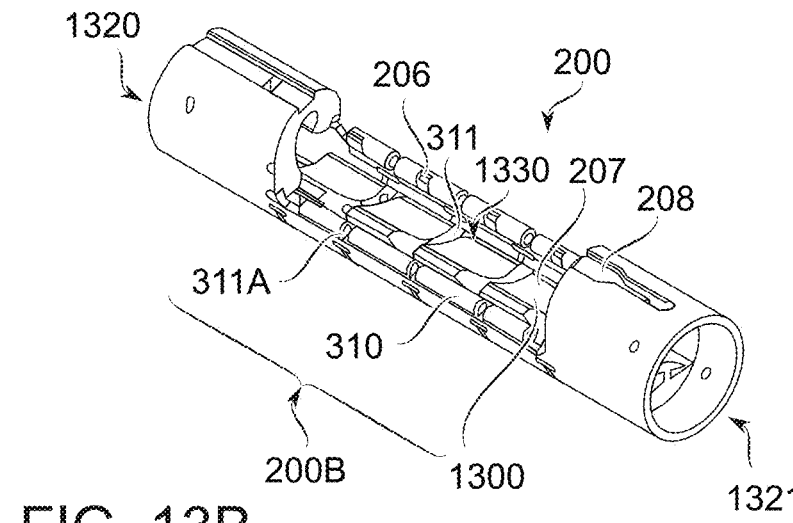
FIG. 13B
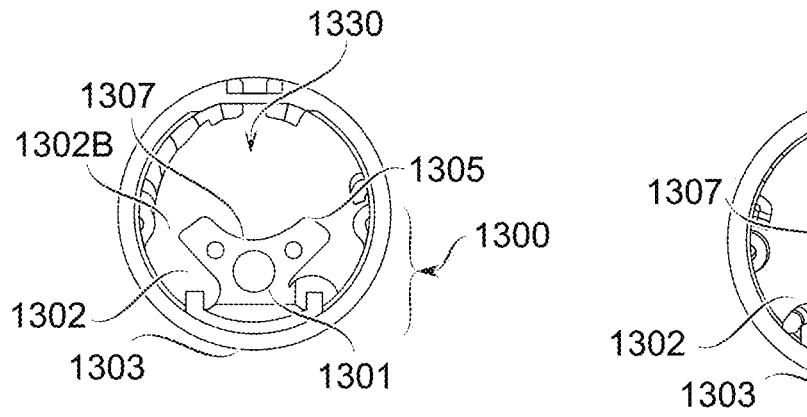
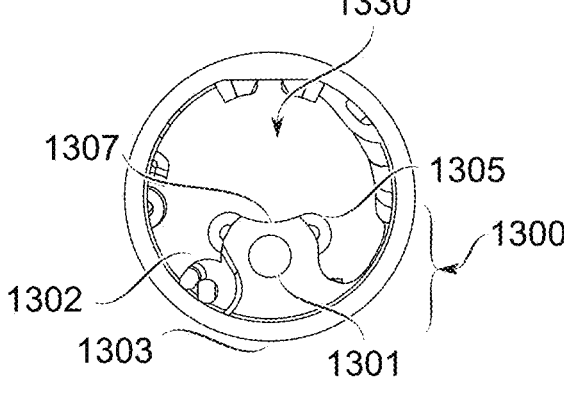
FIG. 13C                FIG. 13D

FIG. 17A                    FIG. 17B

FIG. 17C                    FIG. 17D

START

2200

Insert bougie capsule section to body lumen

2202

Expand suturing space of the
bougie capsule section

2204

Apply suction, collapse body lumen tissue
into the suturing space

2206

Advance needle along the suturing space
by rotation

STOP

TISSUE MANIPULATION WITH AN ENDOLUMINAL GASTROPLASTY DEVICE

RELATED APPLICATIONS

This application is a National Phase of PCT Patent Application No. PCT/IL2020/050041 having International filing date of Jan. 9, 2020, which claims the benefit of priority under 35 USC § 119(e) of U.S. Provisional Patent Application No. 62/790,070 filed on Jan. 9, 2019. The contents of the above applications are all incorporated by reference as if fully set forth herein in their entirety.

FIELD AND BACKGROUND OF THE INVENTION

The present invention, in some embodiments thereof, relates to the field of bariatric surgery and more particularly, to endoluminal placement of gastric sutures.

Obesity and related pathologies such as type 2 diabetes are of growing concern worldwide. Gastrointestinal weight-loss surgery (bariatric surgery) has been shown to be effective in achieving sustained weight loss and amelioration of type 2 diabetes. Gastric volume reductions via open surgical- or laparoscopic sleeve-gastrectomy have proven to be one of the most effective forms of treatment.

Any surgical approach, however, no matter how minimally invasive, will still struggle to meet demand due to the magnitude of this pandemic. Moderately obese patients, as well as vulnerable patients (children, for instance) are underserved patient populations. Procedural cost—which can reach tens of thousands of dollars in the US, for example—is also prohibitive in places worldwide.

Furthermore, surgical procedures themselves are not without risks. Complications such as procedure-related leak, severity of co-morbidities, and surgeon learning curve are but a few of the factors that have been, and will be, limiting extensive adoption of this approach.

In addition to being a relatively non-invasive form of gastric volume reduction procedure, endoluminal gastric sleeve formation carries the potential for reduced risk of leakage from the stomach. Because the stomach itself is optionally left intact, another potential advantage of an endoluminal technique over sleeve formation by surgical resection is reversibility, for example, in case of complications. Devices and methods for endoluminal gastric sleeve formation are described, for example, in: U.S. Patent Publication 2008/0249404 by Mikkaichi et al. filed Dec. 27, 2007; U.S. Pat. No. 6,558,400 to Deem et al. filed May 30, 2001; U.S. Pat. No. 7,896,890 to Ortiz et al. filed Mar. 1, 2011; and U.S. Pat. No. 7,083,629 to Weller et al. filed Aug. 1, 2006.

SUMMARY OF THE INVENTION

There is provided, in accordance with some embodiments of the present disclosure, a bougie capsule section configured for shaping and suturing of tissue of a body lumen from within the body lumen, the bougie capsule section comprising: a capsule body, extending longitudinally between a distal side and a proximal side of the bougie capsule section; an arcuate needle within the capsule body; and a shaft, fitted longitudinally along the capsule body to press against the arcuate needle, and rotatable to drive, by friction between the shaft and the arcuate needle, rotation of the arcuate needle around a longitudinal axis of the capsule body.

In some embodiments, the arcuate needle is a helical needle, and the rotation of the helical needle is accompanied by translation of the helical needle along the longitudinal axis of the capsule body.

In some embodiments, the capsule body defines a helical arrangement of channels along which the helical needle rotates and advances longitudinally; and the shaft presses against the helical needle in at least one position where the shaft crosses the helical arrangement of channels.

In some embodiments, the shaft is radially within an arc of the arcuate needle where the shaft presses against the arcuate needle.

In some embodiments, the shaft is radially outside an arc of the arcuate needle where the shaft presses against the arcuate needle.

In some embodiments, the capsule body and shaft are flexible along a region where the shaft presses against the arcuate needle.

In some embodiments, the arcuate needle comprises a relatively high-friction surface and a relatively low-friction surface; and wherein the shaft presses against the high-friction surface.

In some embodiments, the low-friction surface presses against surfaces of the capsule body.

In some embodiments, the shaft comprises a cable section comprising a plurality of strands, and a pin section comprising a solid piece, positioned along the capsule body where the pin presses against the arcuate needle.

In some embodiments, the pin has a fixed and uniform diameter.

In some embodiments, the pin is tapered.

In some embodiments, the shaft is configured to move longitudinally as it rotates.

In some embodiments, the longitudinal movement of the pin maintains contact of the pin with the needle during a longitudinal movement of the needle.

In some embodiments, the capsule body comprises a plurality of longitudinally aligned lumens arranged along the capsule body, and through which the shaft passes; wherein the shaft is held against the arcuate needle at one or more positions between the longitudinally aligned lumens.

In some embodiments, the capsule body defines a suction clamping domain defined by supporting surfaces positioned along the suction clamping domain, configured to receive the tissue of the body lumen collapsed onto the supporting surfaces upon application of suction to the suction clamping domain while the bougie capsule section is inserted to the body lumen.

There is provided, in accordance with some embodiments of the present disclosure, a method of intraluminal suturing, comprising: rotating a helical needle by frictional interaction with a rotating shaft to advance the helical needle along a bougie capsule section.

In some embodiments, the shaft is fitted longitudinally along the bougie capsule section to press against the helical needle.

There is provided, in accordance with some embodiments of the present disclosure, a bougie capsule section configured for shaping and suturing of tissue of a body lumen from within the body lumen, the bougie capsule section comprising: a capsule body, extending along a longitudinal axis through a suction clamping domain between a distal side and a proximal side of the bougie capsule section; and a suturing space defined by supporting surfaces of the suction clamping domain, configured to receive the tissue of the body lumen collapsed onto the supporting surfaces upon application of suction to the suction clamping domain while the bougie capsule section is inserted to the body lumen; wherein the capsule body comprises articulated segments, configured to change angle with respect to each other to produce a bend in the capsule body.

In some embodiments, the suction clamping domain comprises the articulated segments.

In some embodiments, the articulated segments are longitudinally interconnected in a single continuous piece, and the articulation between segments comprises thinning of material of the single continuous piece to form articulation joints.

In some embodiments, the articulated segments define a helical arrangement of channels, and comprising a helical needle, configured to advance longitudinally as it rotates through the helical arrangement of channels, while the articulated segments are bent.

In some embodiments, the bougie capsule section comprises a shaft, fitted to extend longitudinally through the suction clamping domain and press against the helical needle; and rotatable to drive the rotation of the helical needle by friction between the shaft and the helical needle, while the articulated segments are bent on either side of a position at which the shaft presses against the helical needle.

In some embodiments, the bend is produced by operation of a control member is attached to the capsule body via a longitudinal blocker that extends longitudinally through the suction clamping domain to provide a portion of the supporting surfaces, and longitudinally divides an aperture region leading into the suturing space into separate fenestrations on either side of the longitudinal blocker; and wherein movement of the longitudinal blocker upon the longitudinal movement of the control member produces the bend in the capsule body.

There is provided, in accordance with some embodiments of the present disclosure, a method of intraluminal suturing, comprising: inserting to a body lumen a suction clamping domain of a bougie capsule section configured for shaping and suturing of tissue of a body lumen from within the body lumen; inducing a bend along the suction clamping domain; applying suction to collapse tissue of the body lumen onto supporting surfaces of the suction clamping domain, and into a suturing space within the bent bougie capsule section; and advancing a helical needle through the suturing space and through the bend by a rotation of the helical needle.

There is provided, in accordance with some embodiments of the present disclosure, a bougie capsule section configured for shaping and suturing of tissue of a body lumen from within the body lumen, the bougie capsule section comprising: a capsule body, extending along longitudinal axis through a suction clamping domain between a distal side and a proximal side of the bougie capsule section; and a suturing space defined by supporting surfaces of the suction clamping domain, configured to receive the tissue of the body lumen collapsed onto the supporting surfaces upon application of suction to the suction clamping domain while the bougie capsule section is inserted to the body lumen; wherein the bougie capsule section is expandable by movement of the supporting surfaces.

In some embodiments, expansion of the bougie capsule section increases a cross-sectional size of the suturing space by outward movement of the supporting surfaces.

In some embodiments, the suturing space comprises a dorsal side, a ventral side, and a ventral midline of the ventral side, and wherein at least some of the supporting surfaces attach on sides of the suturing space lateral to the ventral midline, and the supporting surfaces move laterally outward from capsule body upon actuation by a control member.

In some embodiments, the supporting surfaces attach to the capsule body by swivels.

In some embodiments, the suturing space comprises a dorsal side, a ventral side, and a ventral midline of the ventral side, and wherein at least some of the supporting surfaces are surfaces of outriggers attached on sides of the suturing space lateral to the ventral midline, and the outriggers are configured to move the supporting surfaces in a ventral direction from capsule body upon actuation by a control member.

In some embodiments, the outriggers comprise a lattice of separate supports, coupled to each other via their crossings.

In some embodiments, the outriggers comprise a lattice of supports, formed from a piece of shape-memory metal.

In some embodiments, each outrigger comprises a plurality of supports attached to the capsule body by swivels, and joined by a stabilizer bar.

In some embodiments, at least some of the supporting surfaces are surfaces of a longitudinal blocker which is configured to bulge outward from along the ventral midline of the capsule body upon actuation by a control member.

In some embodiments, the bougie comprises a collapsible bougie orientation projection, anchored on a distal side and configured to expand outward upon distal advancing of a control member attached to the collapsible bougie orientation projection.

There is provided, in accordance with some embodiments of the present disclosure, a bougie capsule section of a bougie for intralumenal suturing comprising: a tissue receiving space framed within tissue support structures extending along either side of a longitudinal axis of the capsule section, and a dorsal wall extending between and along the tissue supports at a position dorsally offset from the tissue support structures; wherein an inwardly projecting portion projects from the dorsal wall into the tissue receiving space, dividing it to define channels on either side of the inwardly projecting portion.

In some embodiments, inwardly projecting portion branches to a laterally projecting portion on either side, and the laterally projecting portion defines a hollow between the inwardly projecting portion and the dorsal wall.

There is provided, in accordance with some embodiments of the present disclosure, a bougie capsule section configured for shaping and suturing of tissue of a body lumen from within the body lumen, the bougie capsule section comprising: a capsule body, extending longitudinally to define a suction clamping domain between a distal side and a proximal side of the bougie capsule section; and a suturing space framed by supporting surfaces positioned along the suction clamping domain, configured to receive the tissue of the body lumen collapsed onto the supporting surfaces upon application of suction to the suction clamping domain while the bougie capsule section is inserted to the body lumen; wherein the supporting surfaces comprise a longitudinal blocker that extends longitudinally along the suction clamping domain to longitudinally divide an aperture region leading into the suturing space into separate fenestrations on either side of the longitudinal blocker; and wherein the longitudinal blocker is configured so that movement of the longitudinal blocker produces a bend in the capsule body.

In some embodiments, the longitudinal blocker is removable from over the aperture region to remove the longitudinal division into separate fenestrations.

There is provided, in accordance with some embodiments of the present disclosure, a bougie capsule section configured for shaping and suturing of tissue of a body lumen from within the body lumen, the bougie capsule section comprising: a capsule body, extending longitudinally to define a suction clamping domain between a distal side and a proximal side of the bougie capsule section; and a suturing space framed by supporting surfaces positioned along the suction clamping domain, configured to receive the tissue of the body lumen collapsed onto the supporting surfaces upon application of suction to the suction clamping domain while the bougie capsule section is inserted to the body lumen; wherein the supporting surfaces comprise a closing portion of a longitudinal blocker that extends through a proximal side of an aperture region leading into the suturing space to close the proximal portion of the aperture region; and wherein the longitudinal blocker is configured to be withdrawn proximally, gradually opening the proximal portion of the aperture region.

In some embodiments, the aperture region opened by full withdrawal of the longitudinal blocker comprises a single aperture at least 5 cm long.

In some embodiments, the longitudinal blocker comprises a narrow portion of a longitudinal blocker, narrower than the closing portion, that extends distally from the closing portion and along the suction clamping domain to longitudinally divide an aperture region leading into the suturing space into separate fenestrations on either side of the longitudinal blocker.

Unless otherwise defined, all technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL
VIEWS OF THE DRAWINGS

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced.

Figures 2A, 2B:
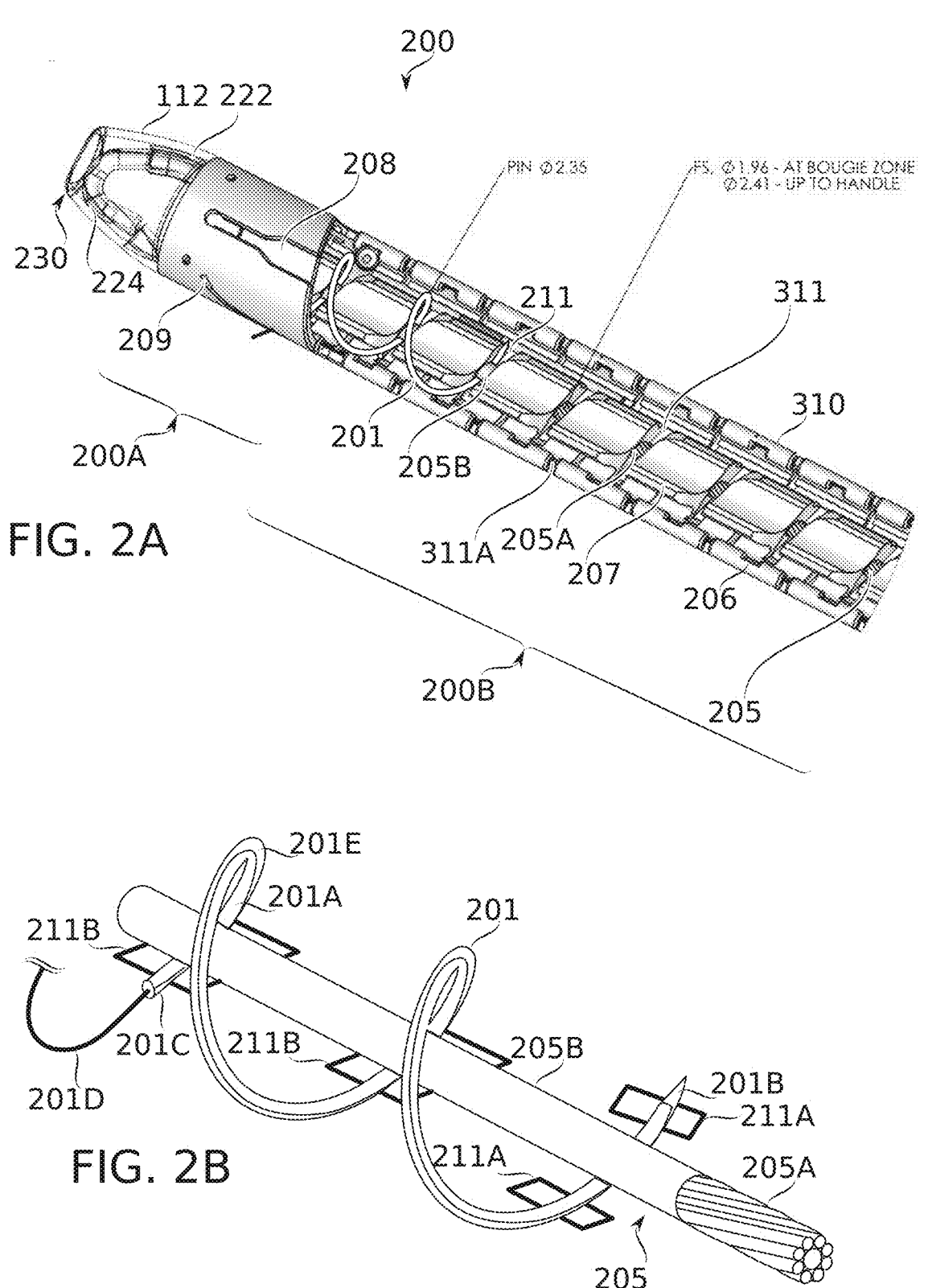
Figure 2C:
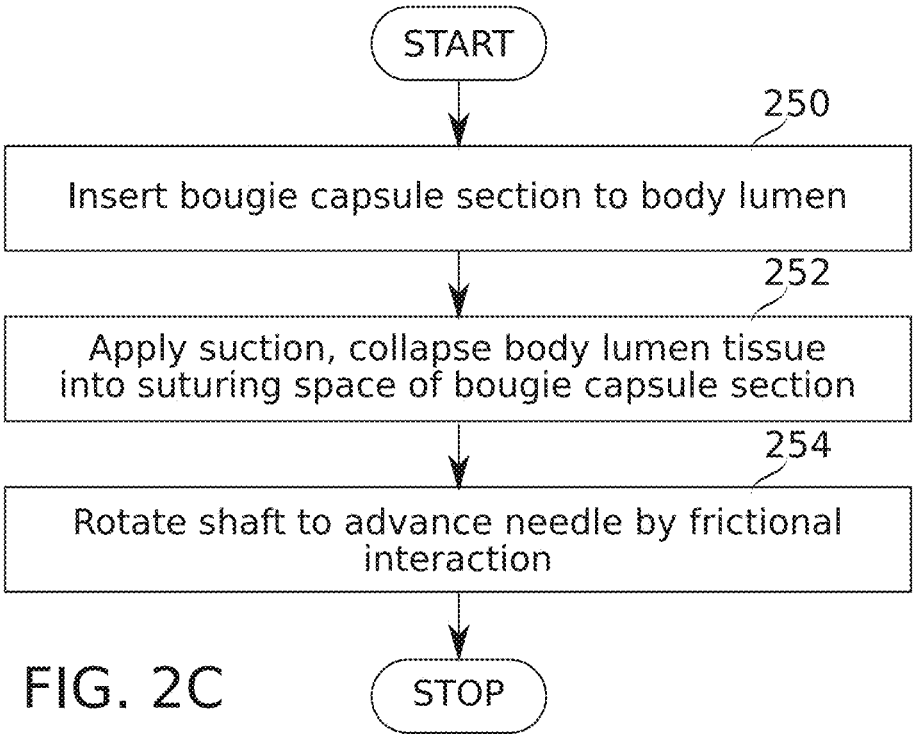
Figures 3A, 3B, 4A, 4B:
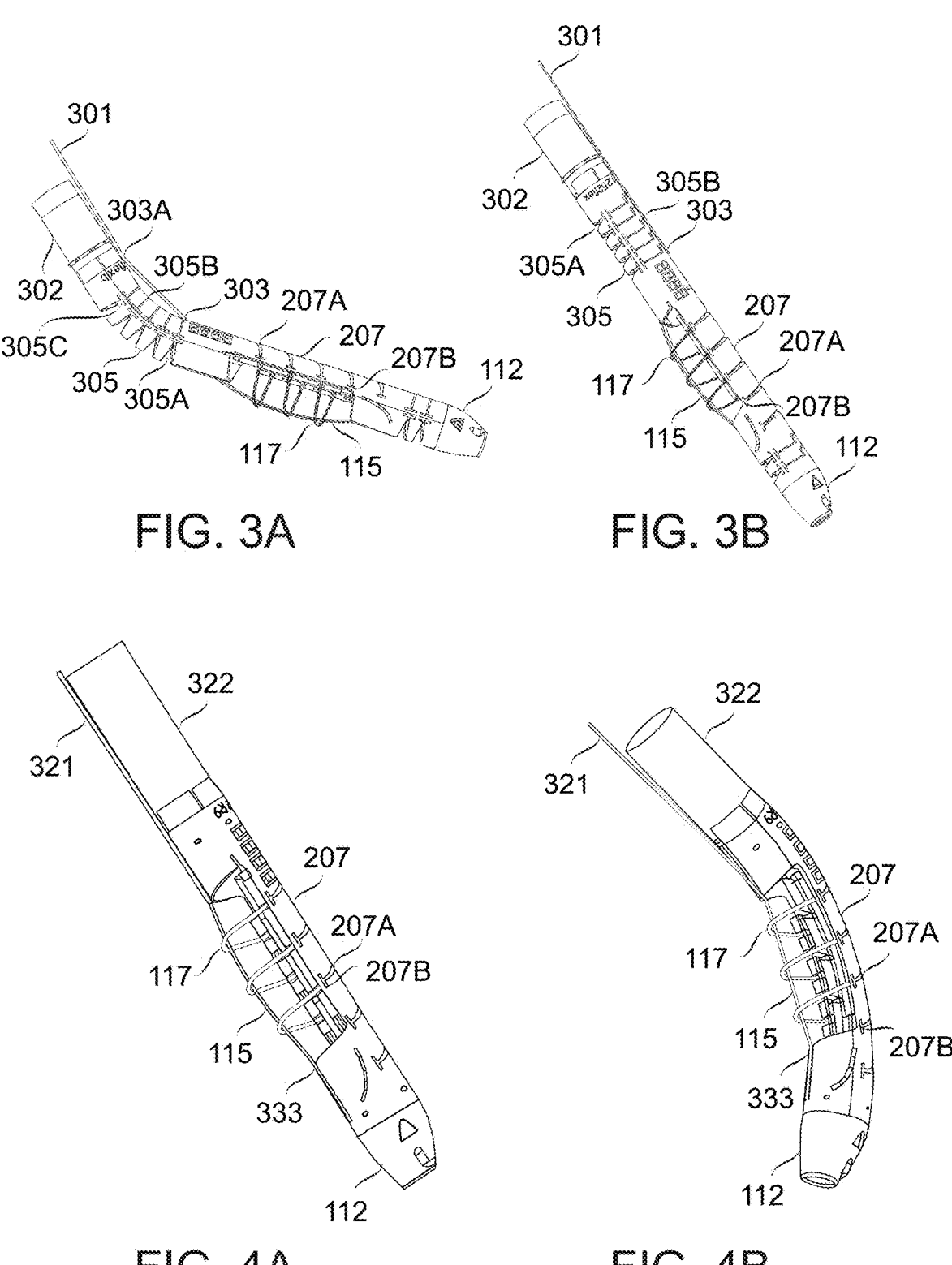
Figures 5A, 5B, 6, 7:
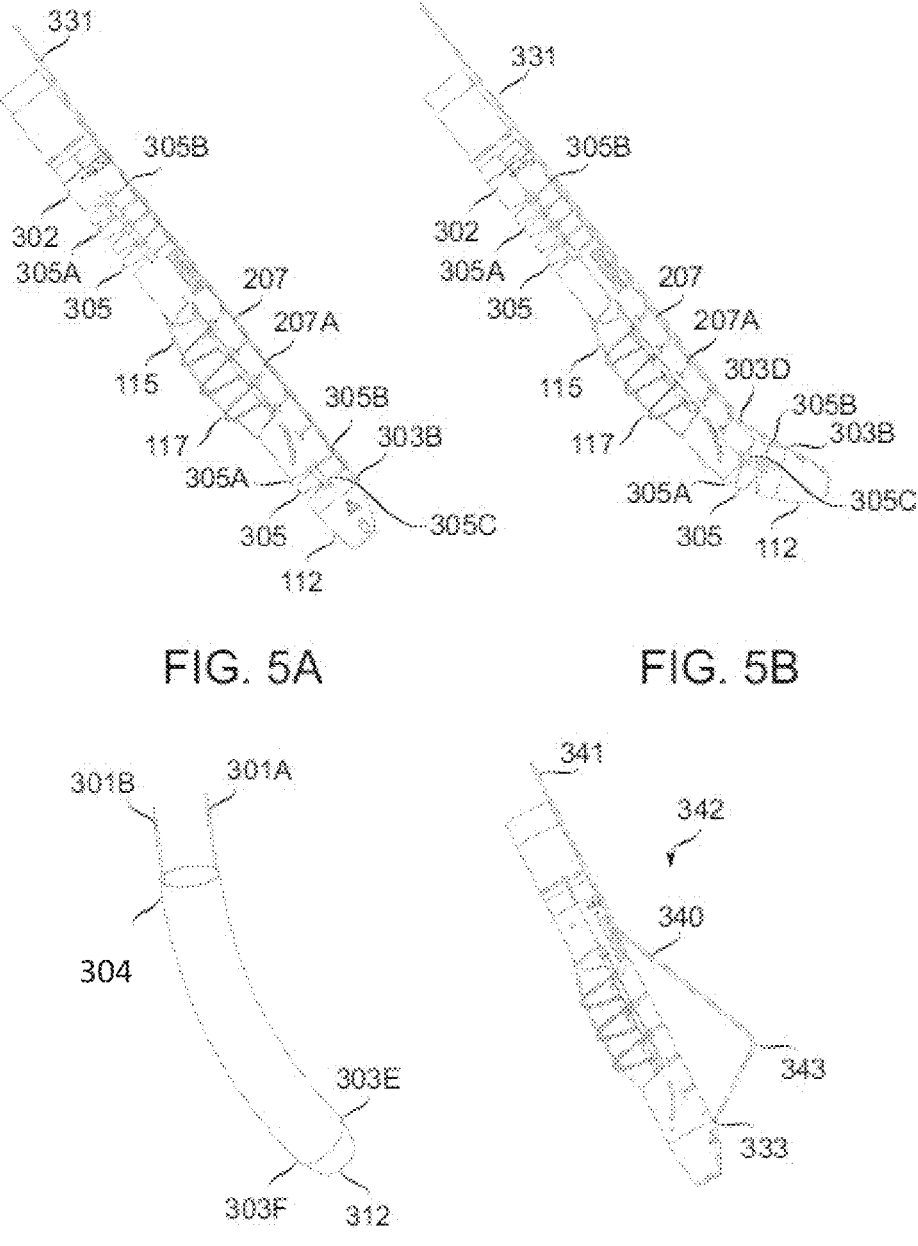
Figure 8A:
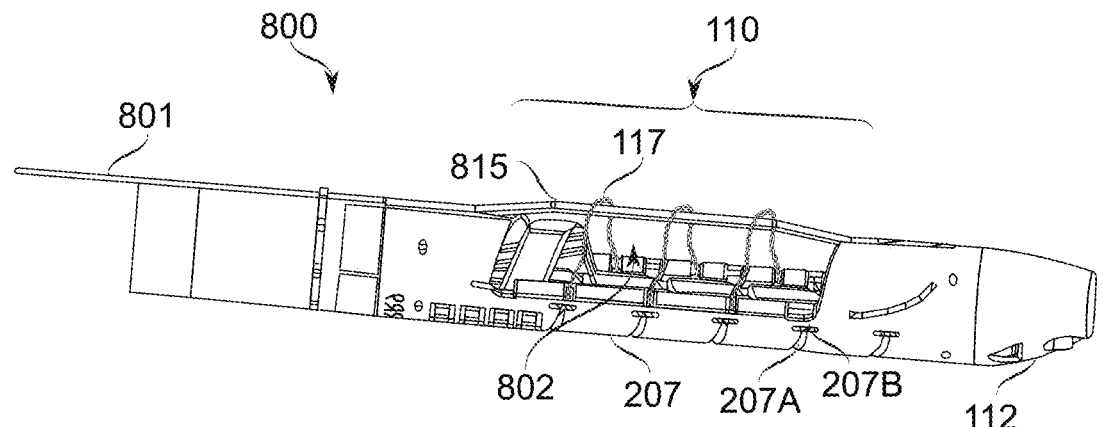
Figure 8B:
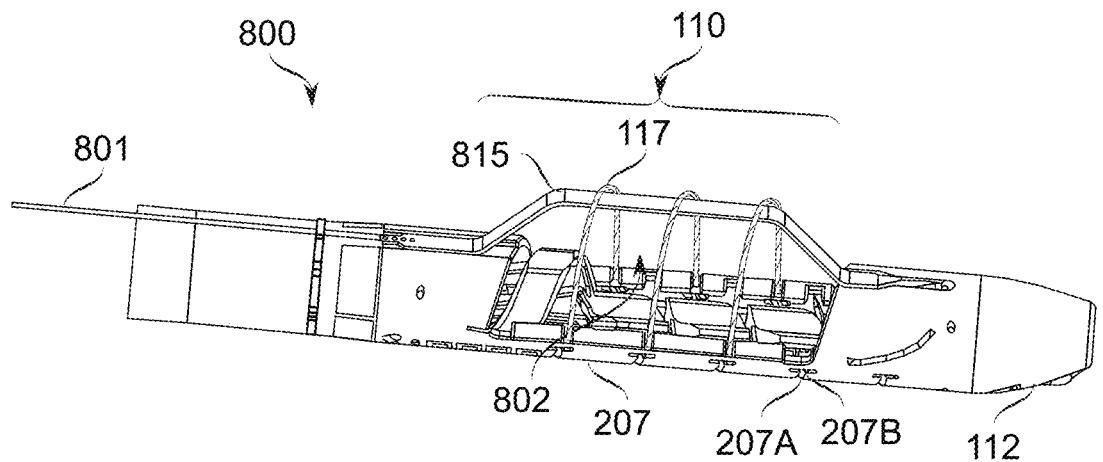
Figure 9A:
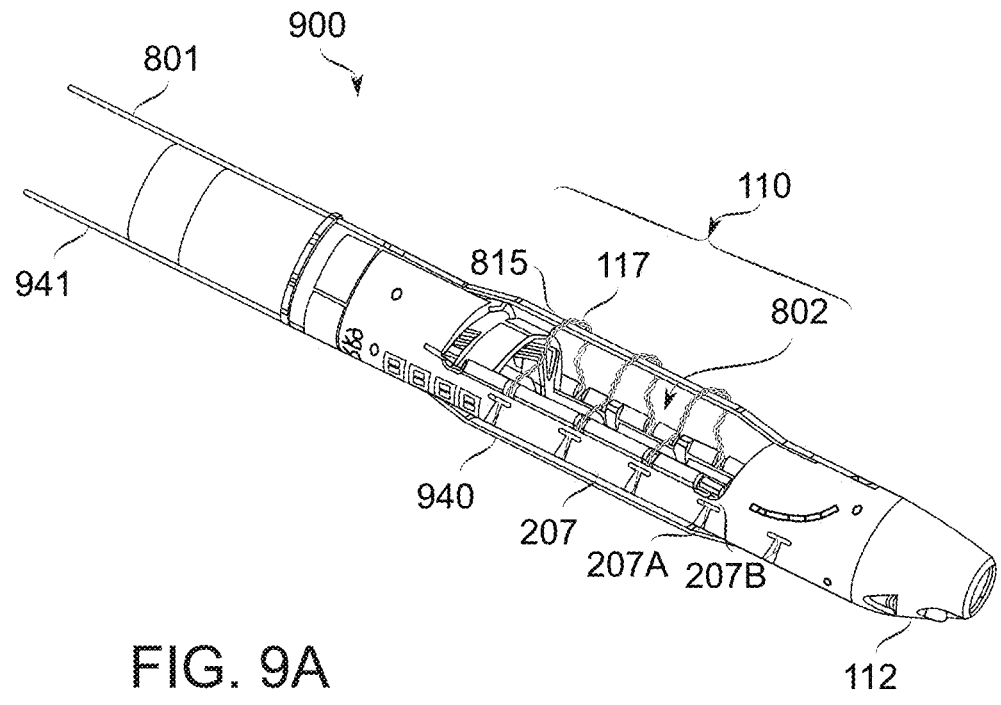
Figure 9B:
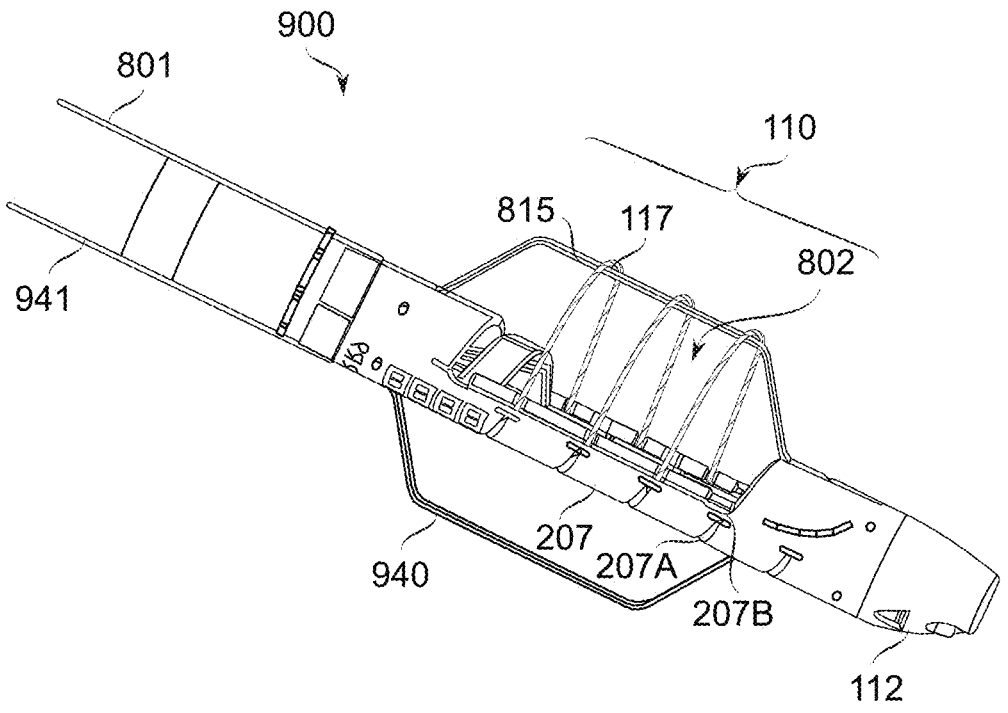
Figure 12A:
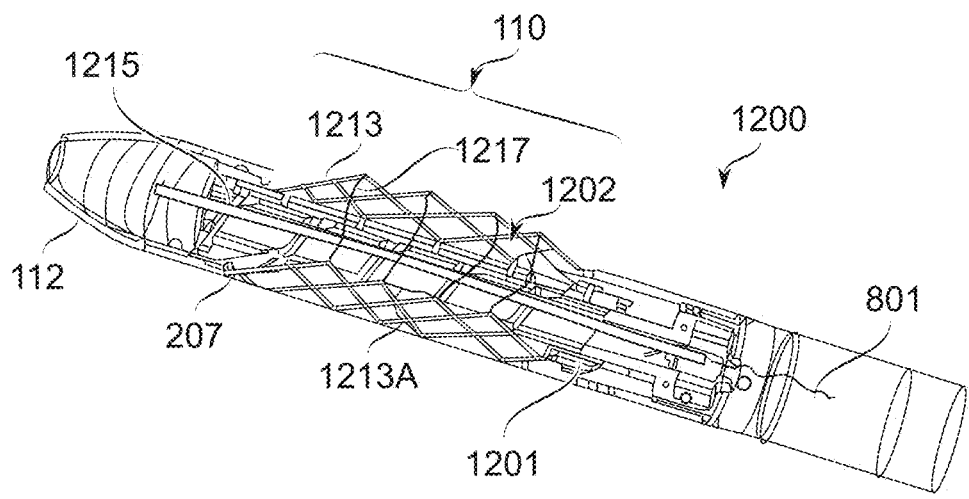
Figure 12B:
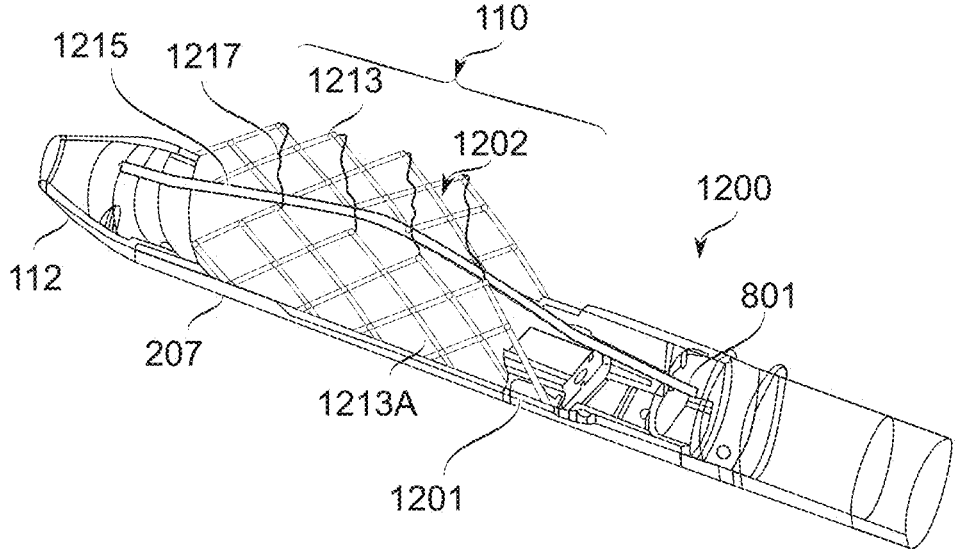
Figure 14A:
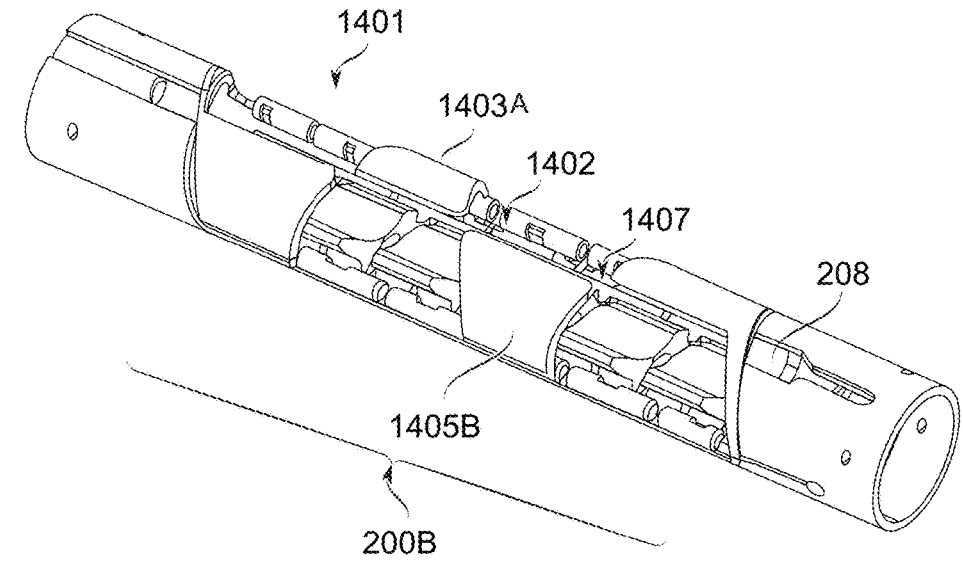
Figure 14B:
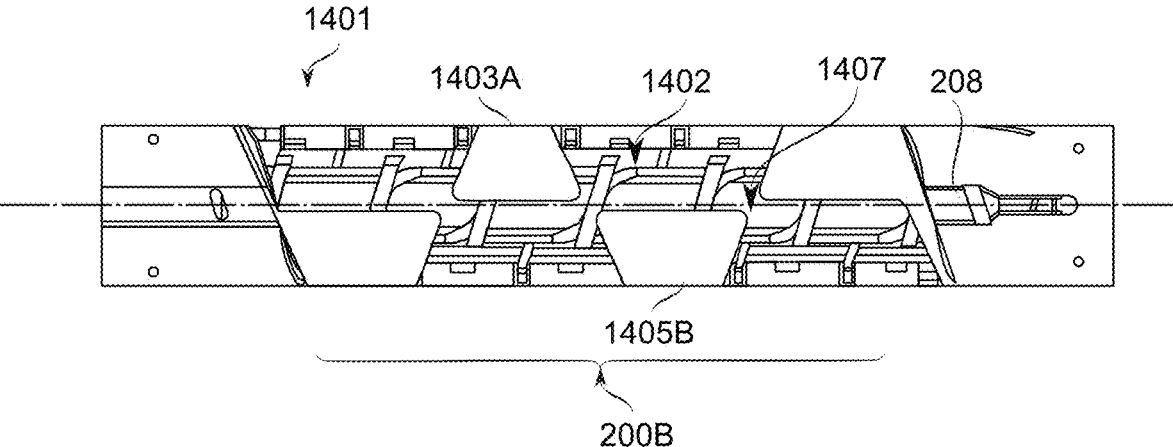
Figures 15A, 15B, 15C:
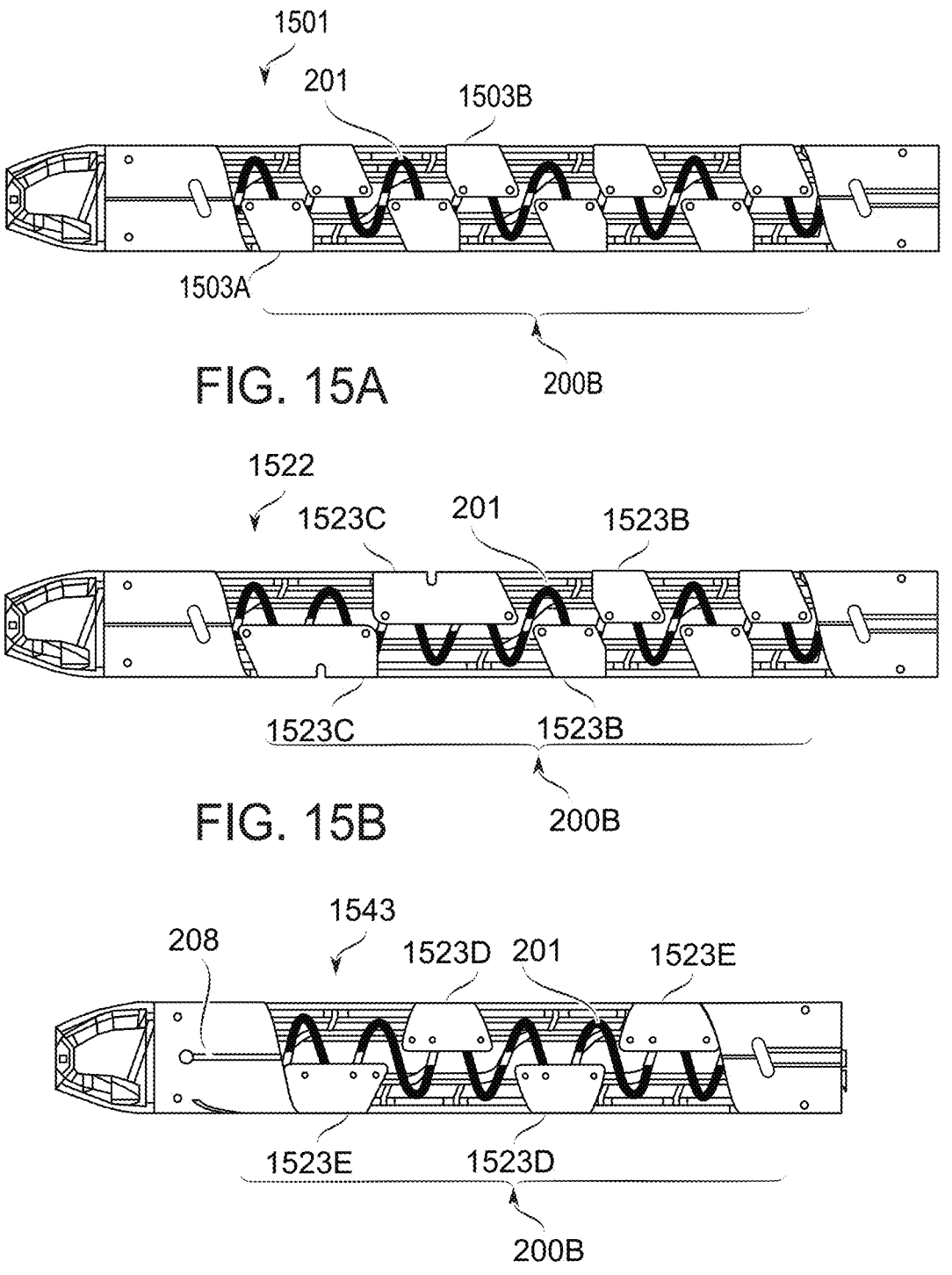
Figure 16A:
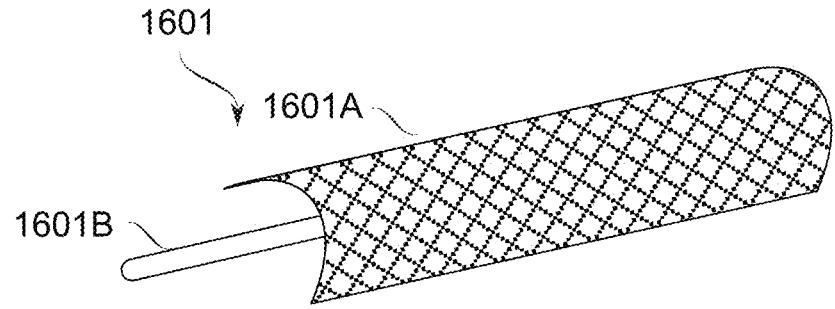
Figure 16B:
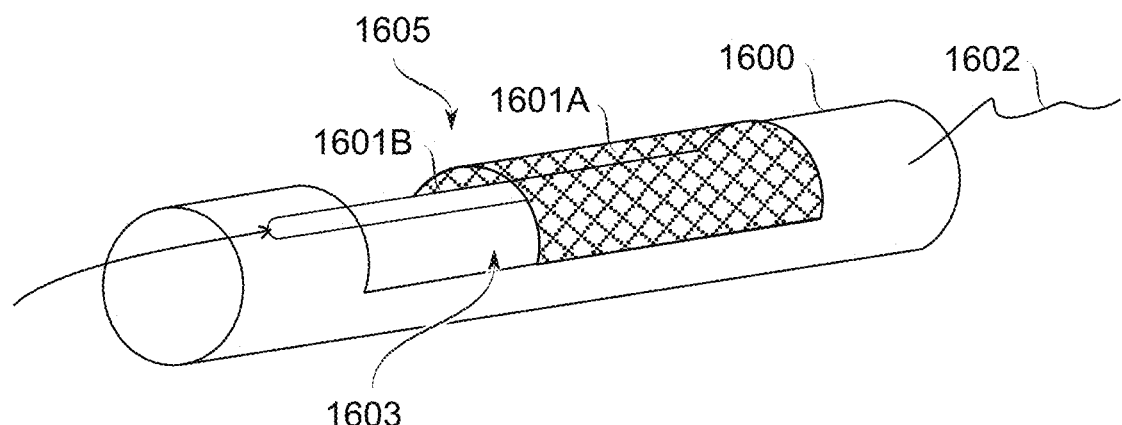
Figure 18A:
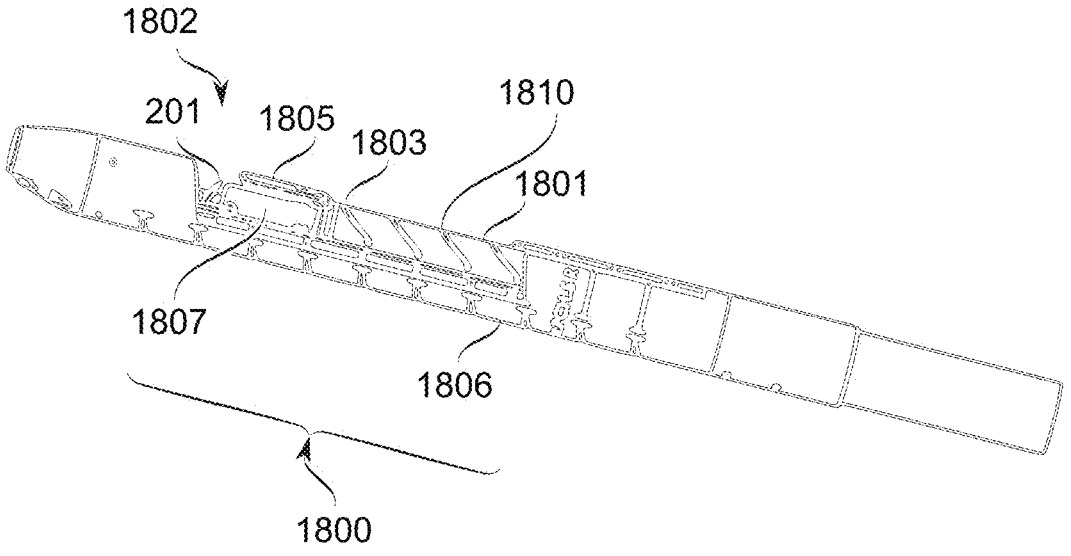
Figure 18B:
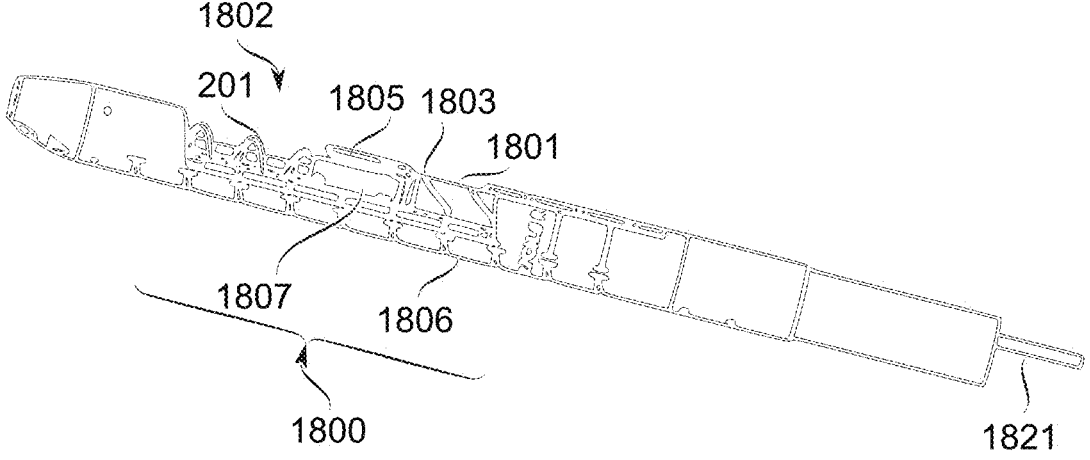
Figure 19:
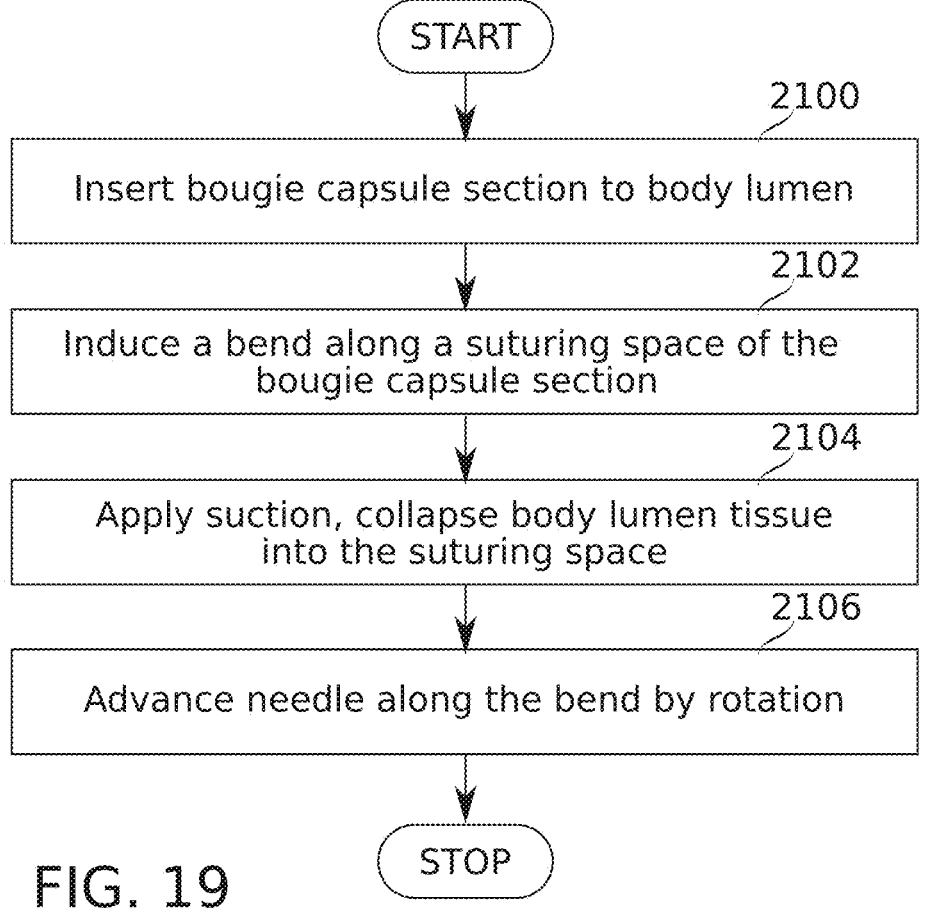
Figure 20:
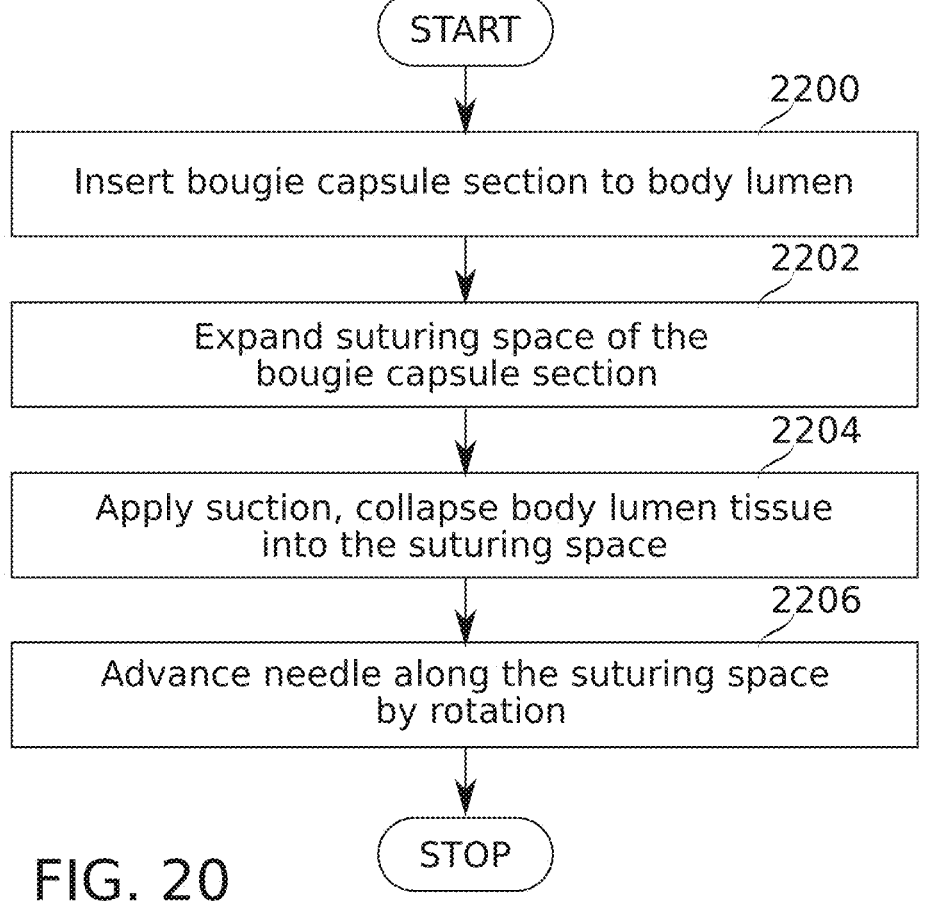

In the drawings:

FIG. 1 schematically represents a bougie configured for shaping and intra-cavity suturing of tissue of a body cavity, according to some embodiments of the present disclosure;

FIG. 2A schematically represents a needle drive configured to drive a helical needle proximally along the interior of a bougie, according to some embodiments of the present disclosure;

FIG. 2B schematically represents a helical needle in relation to a shaft and selected surfaces of a bougie capsule section, according to some embodiments of the present disclosure;

FIG. 2C is a schematic flowchart of a method of intraluminal suturing, according to some embodiments of the present disclosure;

FIGS. 3A-3B schematically represent a flexing mechanism of a bougie capsule section, according to some embodiments of the present disclosure;

FIGS. 4A-4B schematically represent a flexing mechanism of a bougie capsule section, according to some embodiments of the present disclosure;

FIG. 5A-5B schematically represent another flexing mechanism of a bougie capsule section, according to some embodiments of the present disclosure;

FIG. 6 schematically represents an overtube for use with a gastric surgery bougie, according to some embodiments of the present disclosure;

FIG. 7 schematically represents a collapsible bougie orientation projection, according to some embodiments of the present disclosure;

FIGS. 8A-8B schematically represent a bougie capsule section comprising a capsule-expanding blocker, according to some embodiments of the present disclosure;

FIGS. 9A-9B schematically represent a bougie capsule section comprising capsule-expanding blocker with a collapsible bougie orientation projection, according to some embodiments of the present disclosure;

FIGS. 10A-10D schematically represent a bougie capsule section comprising a capsule-expanding blocker, along with a plurality of capsule-expanding flaps, according to some embodiments of the present disclosure;

FIGS. 11A-11D schematically represent a bougie capsule section comprising a capsule-expanding blocker, along with a plurality of capsule-expanding outriggers, according to some embodiments of the present disclosure;

FIGS. 12A-12B schematically represent a bougie capsule section comprising a capsule-expanding blocker, along with a plurality of capsule-expanding outriggers, according to some embodiments of the present disclosure;

FIGS. 13A-13D schematically represent internal structures of a bougie suction clamping domain affecting vacuum distribution, tissue clogging, and/or tissue clamping, according to some embodiments of the present disclosure;

FIGS. 14A-14B schematically represent a suction clamping domain of a bougie capsule section comprising offset fenestrations defined by tissue supports, according to some embodiments of the present disclosure;

FIGS. 15A-15C schematically represent variations of a suction clamping domain of a bougie capsule sections comprising offset fenestrations defined by tissue supports, according to some embodiments of the present disclosure;

FIGS. 16A-16B schematically represent an arrangement of a suction clamping domain allowing progressive unblocking of a fenestration by longitudinal blocker, according to some embodiments of the present disclosure;

FIGS. 17A-17E schematically represent an alternative arrangement of a suction clamping domain allowing progressive unblocking of a fenestration by a longitudinal blocker, according to some embodiments of the present disclosure;

FIGS. 18A-18B schematically represent an alternative arrangement of a suction clamping domain allowing progressive unblocking of a fenestration by a longitudinal blocker according to some embodiments of the present disclosure;

FIG. 19 is a flowchart of a method of intralumenal positioning of a bougie capsule section, according to some embodiments of the present disclosure; and FIG. 20 is a flowchart of a method of intralumenal use of a bougie capsule section, according to some embodiments of the present disclosure.

DESCRIPTION OF SPECIFIC EMBODIMENTS OF THE INVENTION

The present invention, in some embodiments thereof, relates to the field of bariatric surgery and more particularly, to endoluminal placement of gastric sutures.

Overview

An aspect of some embodiments of the present disclosure relates to a needle drive and arcuate needle, configured to drive the arcuate needle along an interior of a bougie body, according to some embodiments of the present disclosure. In some embodiments, the arcuate needle is a helical needle.

In some embodiments, the needle drive comprises a drive shaft securely mounted along a capsule body of the bougie body, so that it presses against the needle. Upon rotation of the shaft, friction between shaft and needle induces the needle to rotate. The needle, in some embodiments, is constrained by a helical arrangement of one or more channels (optionally continuous or interrupted) causing rotational motion to be translated also into longitudinal advance of the helical needle along bougie body.

In some embodiments, the shaft is flexible, and maintains friction drive contact with the helical needle sufficient to drive it, even when the bougie body is bent through a region in which the shaft passes, making contact with the helical needle. In some embodiments, the shaft comprises a dual construction along its longitudinal extent: a cable portion, and a pin portion. The pin portion is the portion making frictional contact with the helical needle. The cable portion, in some embodiments, potentially provides the shaft with flexibility along most of its length. The pin portion, in some embodiments, potentially provides dimensional stability helps to ensure tight and predictable engagement with the needle where the two are in contact.

In some embodiments, an arcuate needle which is not helical (optionally, more than one) is be driven around a circumference of the bougie body (e.g., guided by a circumferential channel of the bougie body), optionally without longitudinal advance.

An aspect of some embodiments of the present disclosure relates to a suction clamping domain of a bougie capsule section, configured with articulations to allow bending, according to some embodiments of the present disclosure.

In some embodiments, the articulations divide articulated segments which are interconnected along a single continuous piece, and the articulation between the segments comprises thinning of material of the single continuous piece to form articulation joints.

In some embodiments, the bougie capsule section includes a helical needle, flexible enough that it can be driven longitudinally (by rotation) along a bend induced in the suction clamping domain. Optionally, the helical needle is driven by frictional interaction with a rotating shaft, which is configured (e.g., clamped into place and with sufficient structural resilience) to maintain a driving connection with the needle even along the region of the bend.

In some embodiments, other parts of the bougie capsule section (e.g., distal and/or proximal to the suction clamping domain) are also articulated, with a bend controllable by movement of a control member.

An aspect of some embodiments of the present disclosure relates to a suction clamping domain of a bougie capsule section, expandable after insertion to a body lumen, according to some embodiments of the present disclosure.

In some embodiments, the suction clamping domain is expandable by movements of one or more flaps and/or outriggers. In some embodiments, the flaps and/or outriggers swivel laterally outward (e.g. away from a ventral midline that extends along a longitudinal axis of the bougie capsule section) and/or expand ventrally (e.g., ventrally along a dorsal-ventral axis of the bougie capsule section perpendicular to the longitudinal axis). It should be understood that references to "longitudinal axis" herein refer to an axis which curves to follow the general curve of the bougie body, if any, and not necessarily an axis which is perfectly straight.

In some embodiments, the suction clamping domain is expandable by flexing movements of a longitudinal blocker, extending longitudinally along the bougie body as a strip or rod of stiff material; for example, a shape-memory metal such as nitinol. In some embodiments, the flexing is controlled by a control member that advances to make the longitudinal blocker bulge, and is retracted to pull the longitudinal blocker flatter again.

An aspect of some embodiments of the present disclosure relates to the division of a tissue-receiving space of a suction clamping domain into separate channels extending along a longitudinal axis of the suction clamping domain.

In some embodiments, a tissue-receiving space defined within a suction clamping domain is partially divided by an inward-protruding portion that protrudes inwardly from a dorsal side of the tissue-receiving space, and then extends laterally within the tissue-receiving space (optionally to form a "branched" or roughly T-shaped structure). A hollow area is left open underneath a laterally extending portion of the inward protruding portion (that is, between the laterally extending portion and the dorsal inner wall of the tissue-receiving space). This hollow region forms a tissue intrusion-restricted channel extending along a longitudinal extent of the suction clamping domain, beyond a main channel of the tissue-receiving space into which tissue is first pulled; e.g., pulled past structures defining fenestrations which lead into the tissue-receiving space from outside the suction clamping domain.

Access to the hollow area by tissue sucked into the tissue-receiving space is restricted to be via a relative narrow opening defined between the laterally-extending portion, and a lateral inner wall of the tissue-receiving space.

Potentially, the structure of the inward-protruding portion provides an advantage by preventing total filling of the hollow area with tissue, and thereby maintaining an open vacuum channel along the longitudinal extent of the tissue-receiving space resistant to tissue blockage.

Another potential advantage of the inward-protruding portion is to serve as a "tissue lock". Tissue sucked into the tissue-receiving space is partially wrapped around the inward-protruding portion (e.g., wrapped around two or more sides of its laterally extending portion, optionally including suction into the hollow area). This wrapping potentially converts suction force into anchoring by convolution of the tissue so that a force applied by a suturing needle (e.g., around an inner circumference of the suction clamping domain) is resisted by an adjacent surface contact of the tissue.

It is noted that, in some embodiments, tissue sucked into the tissue-receiving space is partially blocked from intrusion by structures forming fenestrations at entrances into the tissue-receiving space (e.g., longitudinal blocker, lateral blocker, flaps, and/or outriggers). Tissue intruding into the space past these structures is then further guided, in some embodiments, by the shape of the inward-protruding portion.

Before explaining at least one embodiment of the present disclosure in detail, it is to be understood that the present disclosure is not necessarily limited in its application to the details of construction and the arrangement of the components and/or methods set forth in the following description and/or illustrated in the drawings. Features described in the current disclosure, including features of the invention, are capable of other embodiments or of being practiced or carried out in various ways.

Bougies with Bougie Capsule Section

Reference is now made to FIG. 1, which schematically represents a bougie 100 configured for shaping and intra-cavity suturing of tissue of a body cavity, according to some embodiments of the present disclosure.

Three main sections of bougie 100 are represented as bougie capsule section 101 (distally), bougie main body 102, and bougie control handle 103 (proximally).

Bougie capsule section 101 (herein, a bougie capsule section is also referred to herein as a "capsule"), in some embodiments, comprises a suction clamping domain 110, which in turn comprises one or more fenestrations 111, configured to receive tissue from the body cavity under suction, and to hold and/or position it in preparation for one or more surgical modifications such as suturing. Herein, embodiments of suction clamping domain 110 are described using terminologies distinguished with reference to different structures. The same embodiment is optionally described by more than one of these terminologies.

Aperture-in-a-tubular body terminology: Suction clamping domain 110 comprises a tubular body having an aperture region (that is, a region comprising one or more openings) that opens into a cavity which receives tissue upon application of suction to the cavity.

Spine terminology: Additionally or alternatively, suction clamping domain 110 comprises a spine having a dorsal side and a ventral side. For example, when the aperture of the tubular body becomes large enough, the remaining portion of the tubular body may be readily understood as comprising a spine. Upon application of suction to the region of the spine (in use inserted to a suitable body cavity), tissue is collapsed down onto structures supported along the spine, for example collapsed onto longitudinal blocker(s), lateral blocker(s), flaps, outrigger(s), and/or tissue support(s)).

Space-and-supporting surface terminology: This terminology generalizes from the other two terminologies. Supporting surfaces include surfaces of any structures positioned along the tubular body/spine onto which tissue collapses when suction is applied to the device in use. This may be, for example, the tubular body, the spine, and/or other features such as blockers, flaps, and/or outriggers, for example, as described with various embodiments disclosed herein. The "cavity" of the first terminology is at the same time also a space of this third terminology, defined as the space within the structures which provide supporting surfaces. Additionally or alternatively, this space is positioned along a ventral-facing surface of the "spine" of the second terminology.

The three terminologies should be understood to be equally applicable to all embodiments of the invention. Even with an extremely thin spine (for example), there is still a "cavity" framed within surfaces of the suction clamping domain, albeit the cavity may be a space largely defined by the extents of a framework of open fenestrations (for example, as next explained). Conversely, even with a relatively narrow aperture region in a tubular body, remaining material of the tubular body framing the aperture region can be understood as forming the "spine" of the suction clamping domain, albeit the "ventral-facing surface" in this case is also an internal surface of the tubular body.

Accordingly, for example, it may be equivalently said that upon application of suction to a suction clamping domain, tissue collapses down onto supporting surfaces positioned along its cavity or along its spine. The supporting surfaces comprise, e.g.: surfaces of longitudinal blocker(s), lateral blocker(s), flaps, outrigger(s), and/or tissue support(s); for example, tissue supports formed from material of a tubular body. These different types of supporting structures are described in more detail in relation to the embodiments of the present disclosure.

In another example: a helical needle moving along the "space" (in terms of the third terminology) of the "cavity" (in terms of the first terminology) is equivalently moving along "a ventral-facing surface of the spine" (in terms of the second terminology). In some embodiments, accordingly, the space is also known as a "suturing space".

For the sake of consistency, descriptions herein use the aperture-in-a-tubular body terminology as the primary terminology, even for embodiments in which the spine is narrow. In some relevant examples, specific relative circumferences are described. For example, in some embodiments, a body of bougie capsule section has a circumferential extent in the suction clamping domain of more than half, less than half, more than a third, less than a third, more than a quarter, and/or less than a quarter of a full circumference.

Herein, fenestrations 111 are part of the aperture region of a bougie capsule section 101. Fenestrations, in some embodiments, are configured to be changed in size, shape, and/or topology by actuation of one or more aperture shaping elements. Such fenestrations are also referred to herein as "dynamic" fenestrations.

Aperture shaping element actuation and concomitant changes in dynamic fenestrations 111 are used, in some embodiments, to control one or more aspects of lumen tissue attachment, lumen tissue positioning, or lumen tissue suction depth (e.g., in preparation for suturing); or of tissue release. In some embodiments, tissue release includes release of suturing or other surgical material which may be attached (e.g., sewn, clipped, and/or stapled) to the lumen tissue while it is engaged with the bougie capsule section 101.

Examples of aperture shaping elements, in some embodiments, include a longitudinal blocker 115, and/or lateral blockers 117.

A longitudinal blocker 115, in some embodiments, comprises an element such as a stiffened strip or rod that longitudinally spans at least a portion of suction clamping domain 110, substantially dividing it into two sides of fenestrations 111 which extend longitudinally alongside one another. Longitudinal blocker 115 is optionally removable, re-joining the divided fenestrations 111. This is a potential advantage in tissue and/or suture release; for example to release of the suction clamping domain 110 from suturing which crosses between two body cavity lumen tissue portions, and on an internal side of the longitudinal blocker 115.

Lateral blockers 117, in some embodiments, comprise one or more elements, such as lengths of cord, which cross laterally across suction clamping domain 110. A crossing element creates a division of the suction clamping domain that separates different fenestrations 111 on either side of the element. Lateral blockers 117, in some embodiments, are releasable and/or removable to remove the separation.

Examples of longitudinal blocker 115 and lateral blockers 117 are described, for example, in International Patent Publication No. WO 2016/056016, the contents of which are included by reference in their entirety.

Optionally, a distal tip 112 of bougie capsule section 101 is provided which is transparent, and/or terminates in an aperture large enough (for example, about 6-8 mm in diameter) to pass the distal end of an endoscope probe or other tool out of.

Bougie main body 102, in some embodiments, comprises a tube 121, along which one or more longitudinally extended control members 120 pass, externally and/or internally. In some embodiments, control members 120 interconnect between actuatable elements of the bougie capsule section 101 (e.g., longitudinal blocker 115 and/or lateral blocker 117), and the bougie control handle 103 (e.g., control knobs 122). In some embodiments, tube 121 has an inner diameter large enough (for example, about 6-10 mm) to insert an endoscope probe or other tool through.

Distal tip 112 is preferably provided with a tapered shape to assist in insertion of bougie 100 along a natural body passage such as an esophagus. Bougie capsule section 101 and bougie main body 102 are preferably sized (in diameter and length) and shaped (at least in an insertion configuration) to allow insertion along a natural body passage such as an esophagus to reach a target organ such as a stomach.

Bougie control handle 103, in some embodiments, comprises one or more control knobs 122, configured to control manipulation of control members 120. Optionally, one or more ports 124 are provided, sized to allow insertion of an endoscope or other tool, for passage along the lumen of tube 121 into bougie capsule section 101, and optionally to and/or out of distal tip 112.

Needle Drives

Reference is now made to FIG. 2A, which schematically represents a needle drive configured to drive a helical needle 201 proximally along the interior of a bougie capsule section 200, according to some embodiments of the present disclosure. FIG. 2A shows a bougie capsule section 200 of a bougie 100, which may be configured substantially as described in relation to FIG. 1, with differences/additions as now explained.

Reference is also made to FIG. 2B, which schematically represents helical needle 201 in relation to a shaft 205 and selected surfaces 211 of bougie capsule section 200, according to some embodiments of the present disclosure.

In some embodiments, helical needle 201 is configured to be driven from a distal end 230 of a bougie capsule section 200 by the rotation of a shaft 205 against which helical needle 201 is pressed at one or more locations. As shaft 205 rotates, helical needle 201 rotates along with it. The rotating motion of helical needle 201 is accompanied by advance along a longitudinal axis of bougie capsule section 200; e.g., proximal advance from an initially more distal position.

In some embodiments, bougie capsule section 200 is configured so that friction between shaft 205 and helical needle 201 transfers torque from the rotating shaft 205 to helical needle 201, sufficient for needle advance through tissue while carrying suture.

Optionally, friction is developed in part by pressing helical needle 201 between shaft 205 and one or more surfaces of a body of bougie capsule section 200. These may be, for example, internal surfaces 211 of a dorsal side of bougie capsule section 200 (in the "cutaway tube" interpretation of the device's structure); alternatively described as ventral-side surfaces 211 of a spine of capsule section 200 (in the "spine" interpretation of the device's structure). Optionally, helical needle 201 extends around shaft 205, so that shaft 205 and helical needle 201 rotate in the same circumferential direction. This configuration provides a potential advantage by creating a two-sided pinch immediately at (e.g., as shown for surfaces 211B of FIG. 2B) and/or closely adjacent (e.g., as shown for surfaces 211A) the position of friction interactions between shaft 205 and helical needle 201. Additionally or alternatively, in some embodiments, needle 201 may be pressed against shaft 205 by another method, e.g., by squeezing or pulling from a different location, by being forced through a channel that guides helical needle 201 against shaft 205, or another method.

Alternatively, in some embodiments, shaft 205 is external to the space defined within helical needle 201, so that shaft 205 and helical needle 201 counter-rotate.

In some embodiments, helical needle 201 comprises a relatively high-friction surface 201A, and a relatively low-friction surface 201E. In some embodiments, the two surfaces extend along the curving needle shaft so that part of the needle shaft circumference is higher-friction, and part is lower-friction.

In some embodiments, a surface region 201A of one or both of helical needle 201 and shaft 205 is treated to increase friction. For example, surface 201A of helical needle 201 is optionally roughened. Surface 201A, in some embodiments, includes surface portions that come into contact with cable 205, but not surface portions that come in contact with bougie surface(s) 211, 211A, 211B. Optionally, surface 201A circumferentially comprises about half of the surface area of helical needle 201.

Roughening may be, e.g., by a treatment such as sputter coating or chemical bath, coating with a high-friction material such as a rubber, or another method. The un-roughened surface of the needle 201B may be protected (e.g., by pre-coating) from the roughening treatment, and/or restored to a smooth finish after treatment. Optionally, the un-roughened surface 201E is given a friction reducing treatment, such as a PTFE coating.

Other parts of needle 201 shown in FIG. 2B include suture 201D, suture connection 201C, and needle tip 201B.

Optionally some slippage occurs between movement of helical needle 201 and shaft 205 as it turns. In some embodiments, the maximum average slippage (e.g., average slippage needle 201 experiences while penetrating tissue and pulling a suture behind it) is, for example, up to no more than 20%, 30%, 40%, 50% or 60% slippage. In some embodiments, there is no slippages, so that the minimum average slippage is 0%. Optionally, the minimum average slippage is at least, for example, 5%, 10%, 20%, or 30% slippage.

It should be noted that features described with respect to helical needle 201 moving both rotationally within and longitudinally along bougie capsule section 200 are optionally embodied, changed as necessary, in a non-helical arcuate needle moving rotationally within bougie capsule section 200.

In some embodiments, an arcuate needle which is not helical (optionally, more than one) is to be driven around a circumference of the bougie body (e.g., guided by a circumferential channel of the bougie body), optionally without longitudinal advance.

Shaft 205, in some embodiments, extends from a distal starting point of needle 201 (e.g., within capsule portion 200A), to a proximal side of bougie capsule section 200 and out along the bougie main body 102 to a handle 103 which remains external to a patient during insertion of the bougie to a body cavity such as a stomach. Handle 103, in some embodiments, comprises a knob or other control allowing rotational actuation of the shaft 205.

In some embodiments, shaft 205 comprises a flexible portion 205A, which may be, for example, a twisted cable, e.g., a cable in a 1×8 configuration (one central strand surrounded by 8 outer strands), a 1×12 configuration, or another cable configuration.

In being flexible, flexible portion 205A provides a potential advantage for allowing flexibility of portions of bougie capsule section 200.

For example, in some embodiments, one or more portions of bougie capsule section 200 comprise a plurality of articulated segments, e.g., segments 207. The articulation allows the segments 207 to change angle relative to each other so as to induce a bend along the bougie capsule section 200. In some embodiments, segments 207 are defined by cutouts formed (not necessarily formed by cutting; optionally formed by molding or additive manufacturing methods such as 3-D printing, for example) to leave material between segments 207 sufficient to retain mechanical integrity, but thin enough to flex.

In some embodiments, the cutouts also serve as needle channels 311 through which needle 201 moves as it spirally advances. It should be noted that cutouts can be formed on either side of bougie capsule section 200, for example, cutouts 207A in FIGS. 3A-3B are formed on the bougie capsule section outer side. Cutouts may be formed on both sides. Optionally, cutouts fully penetrate the bougies distal end 200 in some locations. In some embodiments, segments 207 are formed of separate pieces fitted together.

In some embodiments, one or both sidewalls of the suction clamping domain 200B comprise housings 310 for lateral blockers 117 and/or actuatable elements that control the release of the lateral blockers 117. Optionally, gaps 311A between housings 310 increase device flexibility, and/or provide apertures (optionally along with apertures 206) between which lateral blockers 117 cross. For clarity of viewing details of the needle drive mechanism, lateral blockers 117 are not shown in FIG. 2A. Lateral blockers 117 are optionally configured, for example, as shown in any of the figures herein which illustrate them, with additional modifications as necessary for the specifics of the design (for example, use of expandable flaps and/or outriggers).

Optionally, flexible portion 205A directly interacts with needle 201. Optionally, shaft 205 comprises a pin 205B, e.g., a pin 205B which distally terminates shaft 205. Pin 205B, in some embodiments, is stiffer and/or less deformable in cross-section than flexible portion 205B, e.g., comprising a solid rod. This provides a potential advantage for use in a needle drive, by increasing dimensional stability that maintains friction with the needle. This in turn potentially delivers greater and/or more predictable torque to the needle. A rod potentially maintains its shape better than a twisted cable when flexed, so that changing of bougie shape (e.g., as described in relation to FIGS. 3A-5).

In some embodiments, pin 205B is tapered, for example a diameter taper of between 100 µm and 1 mm along a portion of its length. The taper, in some embodiments, allows the pin to be moved (by translation in a direction along the longitudinal extent of suction clamping domain 200B) to a position which selectably gives a tighter or looser friction fit against the needle 201. A tighter fit potentially provides an advantage for increasing the torque which can be applied to the needle 201, while a looser fit potentially provides an advantage to mitigate a case when friction is so high that the pin and/or needle bind.

In some embodiments, a control 122 is configured (e.g., with a screw) to withdraw shaft 205 as it rotates, along a pitch that keeps the needle 201 and pin 205B at matched longitudinal positions, such that the needle 201 maintains contact with the pin 205B. The matching optionally allows some amount of relative longitudinal movement, e.g., to allow for some amount of slippage of the needle 201 against pin 205B without pin 205B becoming disengaged with needle 201.

Other elements shown in FIG. 2A include:

Channel 208; configured, in some embodiments, as part of the anchor of one side of a longitudinal blocker 115 (not shown).

Channel 209; configured, in some embodiments, to hold a distal end of a control member (e.g., a wire) used to anchor longitudinal blocker 115. For example, a wire passes distally through channel 209, then optionally across (e.g., inside) the bougie body to an aperture of the longitudinal blocker 115 held in channel 208. To unlock longitudinal blocker 115, the wire is withdrawn proximally along channel 209.

Channels 224 and 222, along which suture may move as it is pulled along by a needle 201 to which it is attached. Optionally, channel 222, 224 are made of a low-friction polymer material, for example, polytetrafluoroethylene (PTFE). Optionally, suture is rolled/folded and stored within channel 222 and/or 224. Optionally, suture is stored elsewhere (for example, rolled on a bobbin and/or stored extending back along a longitudinal length of bougie 100).

Reference is now made to FIG. 2C, which is a schematic flowchart of a method of intraluminal suturing, according to some embodiments of the present disclosure.

The flowchart begins, and at block 250, in some embodiments, a suction clamping domain 200B of a bougie capsule section 200 is inserted to a body lumen (such as a stomach).

At block 252, in some embodiments, suction is applied. Under the force of suction, body lumen tissue is collapsed onto supporting surfaces of the suction clamping domain 200B. Some of the body lumen tissue is sucked into a suturing space defined at the level of suction clamping domain 200B by apertures between the supporting surfaces; for example, sucked into the suturing space through fenestrations. In some embodiments, the collapsed tissue is arranged so that tissue from one portion of a body lumen wall is sucked into a left lateral set of fenestrations, and tissue from another (e.g., facing) portion of a body lumen wall is sucked into a right lateral set of fenestrations. Optionally, the midline between right and left is defined by a longitudinal blocker 115.

At block 254, in some embodiments, a shaft 205 is rotated. Shaft 205 presses against a surface of needle 201, so that rotation of shaft 205 induces, by frictional interaction, a rotation of needle 201. Needle 201, upon rotating, is also longitudinally translated along suction clamping domain 200B.

Steering Mechanisms

Reference is now made to FIGS. 3A-3B, which schematically represent a flexing mechanism of a bougie capsule section 302, according to some embodiments of the present disclosure. Reference is also made to FIG. 5A-5B, which schematically represent another flexing mechanism of a bougie capsule section 302, according to some embodiments of the present disclosure.

Bougie capsule section 302 (an example of bougie capsule section 101), in some embodiments, comprises a distal section of a bougie 100. It should be understood that the flexing mechanism described in relation to FIGS. 3A-3B and/or FIGS. 5A-5B is optionally provided, changed as necessary, together with features of any other bougie capsule section of a bougie 100 described herein. Each mechanism (the more proximal mechanism of FIGS. 3A-3B, and the more distal mechanism of FIGS. 5A-5B) is optionally provided alone, or the two may be provided in combination.

The flexing mechanism, in some embodiments, operates by longitudinal movement (e.g. pulling or pushing; shortening or lengthening) a control member 301, 331 to introduce bending along a segmented portion of bougie capsule section 302. In FIG. 3B, the control member 301 is at its relaxed length, and bougie capsule section 302 is straight. In FIG. 3A, the control member 301 is shortened, and bougie capsule section 302 is curved along a portion of its body. In FIG. 5A, the control member 331 is at its relaxed length, and bougie capsule section 302 is straight. In FIG. 5B, the control member 331 is shortened, and bougie capsule section 302 is curved nearer to its distal end.

The flexing mechanism, in some embodiments, comprises control member 301 and/or 331 (examples of control members 120), and at least one control attachment 303, 303B of control member 301, 331 to bougie capsule section 302 (optionally one or more additional attachments 303A, 303D are provided, e.g., to help direct bending forces). Also provided are one or more segments 305 defined by cutouts 305A which are formed from a single continuous piece interconnecting segments 305, e.g., by cutting, molding, and/or additive manufacture. Thinned material left alongside the cutouts 305A acts as an articulation joint. In some embodiments, segments 305 are formed of separately manufactured pieces fitted together, with the cutouts 305A defined by gaps between the fitted pieces. Optionally, cutouts 305B are provided on an opposite side of the bougie capsule section 302.

In some embodiments, the segment cutouts 305A are positioned on a side of bougie capsule section 302 opposite control member 301, 331 (a ventral side, as shown in FIGS. 3A-3B and 5A-5B), so that shortening of control member 301, 331 (e.g., pulling from handle 103) causes expansion on that side. In some embodiments, the segment cutouts 305B are positioned on a side of bougie capsule section 302 the same as control member 301, 331 (a dorsal side, as shown in FIGS. 3A-3B and 5A-5B), so that shortening of control member 301 (e.g., pulling from handle 103) causes compression on that side. Hinges 305C, in some embodiments, are defined with a relatively thin dorsal-ventral dimension (for example, 1-3 mm). Optionally, hinges 305C, 207B are defined by segmenting material on the lateral sides of bougie capsule section 302 with additional cutout slots.

In some embodiments the functions of control members 301, 331 are combined. For example control member 331 is attached so that shortening/pulling also bends the segments 305 which are located more proximally. Optionally, both the proximal segments and the distal segments are operated together. Optionally, the one set of segments is provided on more flexible hinges 305C, so that bending occurs first there, and then, with greater shortening/pulling force, on the other set of segments.

Also indicated in FIGS. 3A-3B and 5A-5B are positions of segments 207, cutouts 207A, distal tip 112, longitudinal blocker 115, and lateral blockers 117, which operate, for example, as described in relation to FIG. 1.

Reference is now made to FIGS. 4A-4B, which schematically represent a flexing mechanism of a bougie capsule section 322, according to some embodiments of the present disclosure.

Bougie capsule section 322 (an example of bougie capsule section 101), in some embodiments, comprises a distal section of a bougie 100. It should be understood that the flexing mechanism described in relation to FIGS. 4A-4B is optionally provided, changed as necessary, together with features of any other bougie capsule section of a bougie 100 described herein, including together with other flexing mechanisms.

The flexing mechanism, in some embodiments, operates by shortening or lengthening a control member 321 to introduce bending along a segmented portion of bougie capsule section 322. In FIG. 4A, the control member 321 is at its relaxed length, and bougie capsule section 302 is straight. In FIG. 4B, the control member 321 is shortened, and bougie capsule section 302 is curved. Segmentation of a portion of bougie capsule section 322 into segments 207 separated by cutouts 207A (and optionally other cutouts not shown, e.g., cutouts internal to bougie capsule section 322) is optionally as described in relation to other figures herein, for example FIGS. 2A and/or 3A-3B.

In some embodiments, control member 321 is attached to longitudinal blocker 115, such that shortening (pulling on) control member 321 causes longitudinal blocker 115 to pull on bougie capsule section 322 at attachment 333, and in turn introduce a curvature to bougie capsule section 322. It should be noted that longitudinal blocker 115 optionally is released from attachment 333 by operation of a separate mechanism (e.g., via a different control member 120). Once released from attachment 333, control member 321 operates to withdraw longitudinal blocker 115, rather than to introduce curvature to bougie capsule section 322. In some embodiments, longitudinal blocker 115 is released by pulling on control member 321 past/above a predefined position/tension, and that predefined position/tension is predefined so that bending can be reliably induced without accidentally triggering attachment release.

Also indicated in FIGS. 4A-4B are positions of segments 207, cutouts 207A, distal tip 112, and longitudinal blocker 115, which operate, for example, as described in relation to FIG. 1.

Reference is now made to FIG. 19, which is a flowchart of a method of intralumenal positioning of a bougie capsule section, according to some embodiments of the present disclosure.

The flowchart begins, and at block 2100, in some embodiments, a suction clamping domain 200B of a bougie capsule section 200 is inserted to a body lumen (such as a stomach).

At block 2102, in some embodiments, a bend is induced along a suturing space defined by supporting surfaces of the suction clamping domain 200B. In some embodiments, the bend is induced by longitudinal movement of a control member 120. Optionally, the control member 120 induces bending by movement of a longitudinal blocker 115. In some embodiments, the suction clamping domain 200B comprises articulated segments 207, and the bending comprises induction of a change in the angle(s) at which the articulated segments 207 meet.

At block 2104, in some embodiments, suction is applied. Under the force of suction, body lumen tissue is collapsed onto supporting surfaces of the suction clamping domain 200B. Some of the body lumen tissue is sucked into a suturing space defined at the level of suction clamping domain 200B by apertures between the supporting surfaces;

for example, sucked into the suturing space through fenestrations. In some embodiments, the collapsed tissue is arranged so that tissue from one portion of a body lumen wall is sucked into a left lateral set of fenestrations, and tissue from another (e.g., facing) portion of a body lumen wall is sucked into a right lateral set of fenestrations. Optionally, the midline between right and left is defined by the longitudinal blocker 115.

Optionally, in some embodiments, the method of FIG. 19 continues with block 2106, in which a helical needle 201 is longitudinally advanced by rotation along the bent portion of the suturing space. In some embodiments, helical needle 201 is longitudinally advanced by frictional contacts with a rotating shaft 205, wherein the frictional contacts occur at positions along the bent portion of the suturing space.

Reference is now made to FIG. 6, which schematically represents an overtube for use with a gastric surgery bougie, according to some embodiments of the present disclosure.

Overtube 304, in some embodiments, is sized to pass along an access way (e.g., an esophagus) to a body cavity (e.g., a stomach) targeted for suturing, with the eventual orientation of aperture 312 within the body cavity being controlled in part by the direction and degree of a bend induced to the overtube, e.g., by use of control members 301A, 301B.

Overtube 304 is sized to accept bougie capsule section 101 passing within it from a proximal end, and out through aperture 312 at a distal end of overtube 304. In use, overtube 304 bending and position has the effect of adjusting the angulation of bougie capsule section 101 as it passes out of overtube aperture 312. This is a potential advantage for steering bougie capsule section 101 to an intended suturing site within a body cavity such as a stomach, optionally without or auxiliary to the use of a steering mechanism provided on the bougie 100 itself.

In some embodiments, control members 301A, 301B (examples of control member 120) are affixed to the body of a flexible overtube 304. Shortening (pulling on) one of the control members 301B, 301A operates to bend the overtube in the direction of the side on which the control member attaches (e.g., control members 301A and 301B attach at attachments 303E and 303F, respectively). The overtube 304 is optionally locked into position once a suitable bend has been introduced.

Orientation Projections

Reference is now made to FIG. 7, which schematically represents a collapsible bougie orientation projection 340 according to some embodiments of the present disclosure.

In some embodiments, orientation projection 340 is configured to be controllably extended from the side of bougie distal end 342, e.g., by manipulation of control member 341 (which is an example of a control member 120). When extended within a suitably shaped body cavity, (e.g., a body cavity such as a stomach which lacks radial symmetry so that it is longer in one direction than in another) orientation projection 340 helps to force the bougie distal end 342 into a predetermined orientation relative to the body cavity. Optionally, orientation projection 340 also operates to stretch out tissue of the body cavity, e.g., to position it in preparation for attachment by suction.

In some embodiments of the present disclosure, bougie 100 is provided with a collapsible orientation projection 340. By advancing (distally) control member 341, orientation projection 340, which is normally stowed collapsed against the side of bougie capsule section 342, is induced to protrude. In some embodiments, orientation projection 340 is formed of a shape memory alloy such as nitinol. It takes up a predetermined shape, e.g., comprising a bend 343, upon receiving sufficient slack from distally advancing control member 341 to allow it to relax into its preformed shape. Optionally, the shape is at least partially pushed into shape, e.g., by generating pressure of orientation projection 340 against attachment 333.

Also indicated in FIGS. 2A, 3A-5B, and 8A-13B_are positions of segments 207, cutouts 207A, distal tip 112, longitudinal blocker 115, and lateral blocker 117, which operate, for example, as described in relation to FIG. 1.

In some embodiments, projection 340 is also controllable by twisting to change the relative circumferential positions of its distal and proximal ends. Potentially, this assists in device positioning, for example, by inducing pressing against a tissue wall to re-orient the bougie distal end 342.

Expandable Capsule Sections

Reference is now made to FIGS. 8A-8B, which schematically represent a bougie capsule section 800 comprising a capsule-expanding blocker 815, according to some embodiments of the present disclosure. Reference is also made to FIGS. 9A-9B, which schematically represent a bougie capsule section 900 comprising capsule-expanding blocker 815 with a collapsible bougie orientation projection 940, according to some embodiments of the present disclosure. Bougie capsule sections 800, 900 are examples of bougie capsule section 101.

In some embodiments, a capsule-expanding blocker 815 is configured to change shape (e.g., bulge) to expand a size of suction clamping domain 110; for example, to open fenestrations 802 of the aperture domain 110 to a larger size. This has the potential advantage of increasing the amount and/or depth of lumen wall tissue that is held (potentially more securely) under vacuum. For example, by lengthening each fenestration 802 (in a direction both laterally across and radially outward from suction clamping domain 110) a greater depth of tissue can potentially be taken in by suction at the positions where needle penetration (e.g., by a helical needle 201) will occur during suturing.

In some embodiments, a doubled thickness of tissue is drawn in to a fenestration 802 by vacuum to a sufficient depth as to allow the needle to fully penetrate inside-to-outside, and then inside-to-outside the body lumen tissue (e.g., stomach wall) as it passes through the "bite" of tissue which has been drawn into the fenestration by vacuum.

In some embodiments, capsule-expanding blocker 815 comprises an instance of a longitudinal blocker 115, arranged to extend longitudinally along a midline of the bougie capsule section 800 which is configured to change shape by bulging outward under external control. For example, control member 801 (an example of a control member 120) advances distally to allow capsule-expanding blocker 815 to expand, and/or is pulled proximally (shortened) to flatten it. Capsule-expanding blocker 815 optionally comprises a shape memory alloy such as nitinol, which returns to a predetermined shape upon being allowed to relax when control member 801 advances (lengthens). Optionally, control member 801 actively pushes blocker 815.

Optionally, lateral blockers 117 are long and loose enough when longitudinal blocker 815 is in the collapsed configuration to allow longitudinal blocker 815 to expand. Alternatively, they are initially strung more tightly, and slack is payed out as longitudinal blocker 815 expands. In some embodiments, the lateral blockers 117 are adjustable in tension to accommodate different degrees of expansion of longitudinal blocker 815. In some embodiments, a control member 120 (not shown) is provided that can be manipulated to tighten/loosen slack in lateral blockers 117.

In some embodiments, a collapsible bougie orientation projection 940 is provided along with capsule-expanding blocker 815, for example as shown collapsed in FIG. 9A, and expanded in FIG. 9B. Collapsible bougie orientation projection 940 is operable, in some embodiments, by manipulation of control member 941, substantially as described in relation to collapsible bougie orientation projection 340 and control member 341 in relation to FIG. 7. Optionally, a spacing of bougie capsule section 900 from a nearby tissue wall is controlled by a degree of expansion of bougie orientation projection 340, pressing against the nearby tissue wall.

Figures 10A, 10B, 10C, 10D:
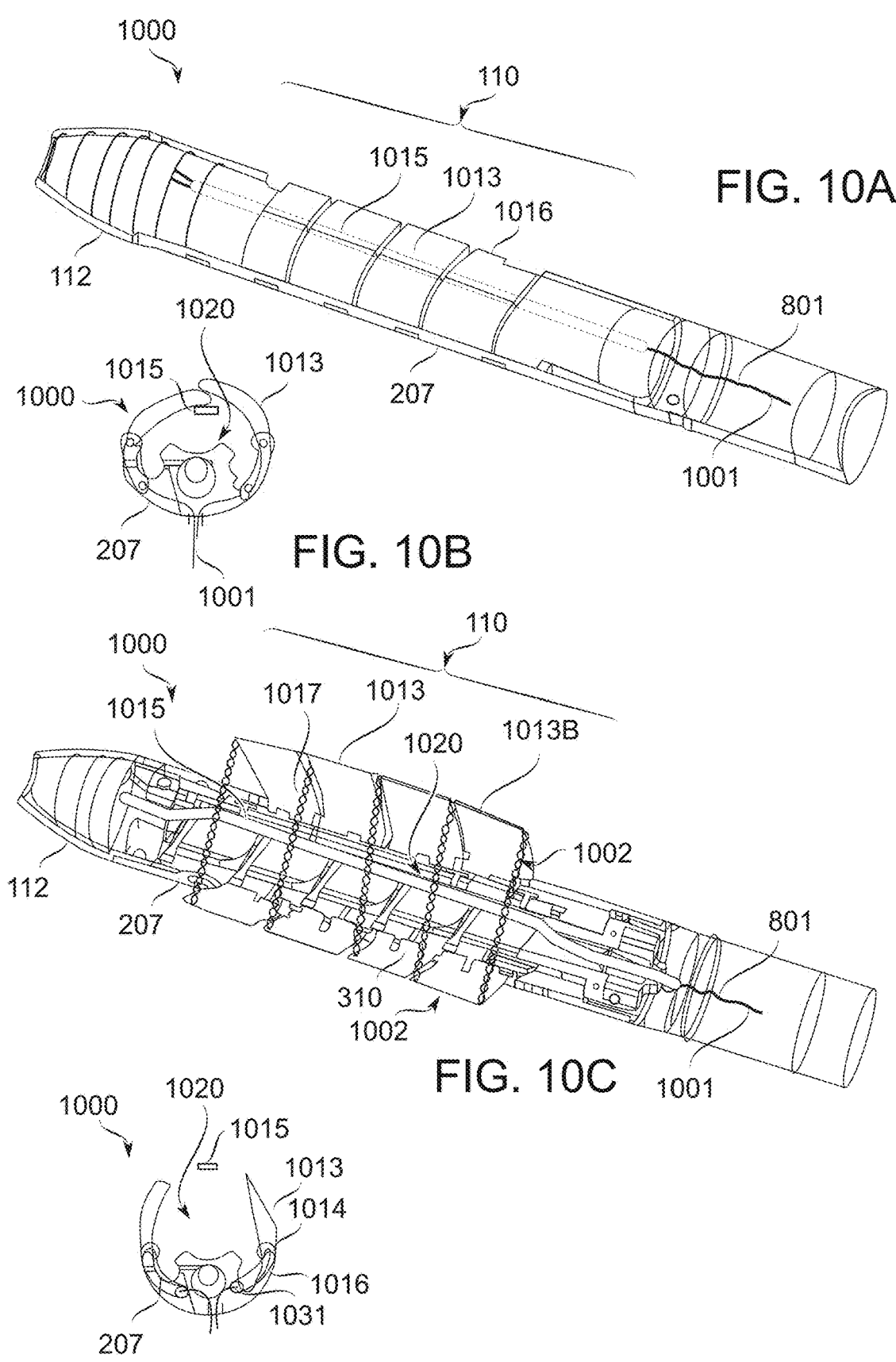
Figures 11A, 11B, 11C, 11D:
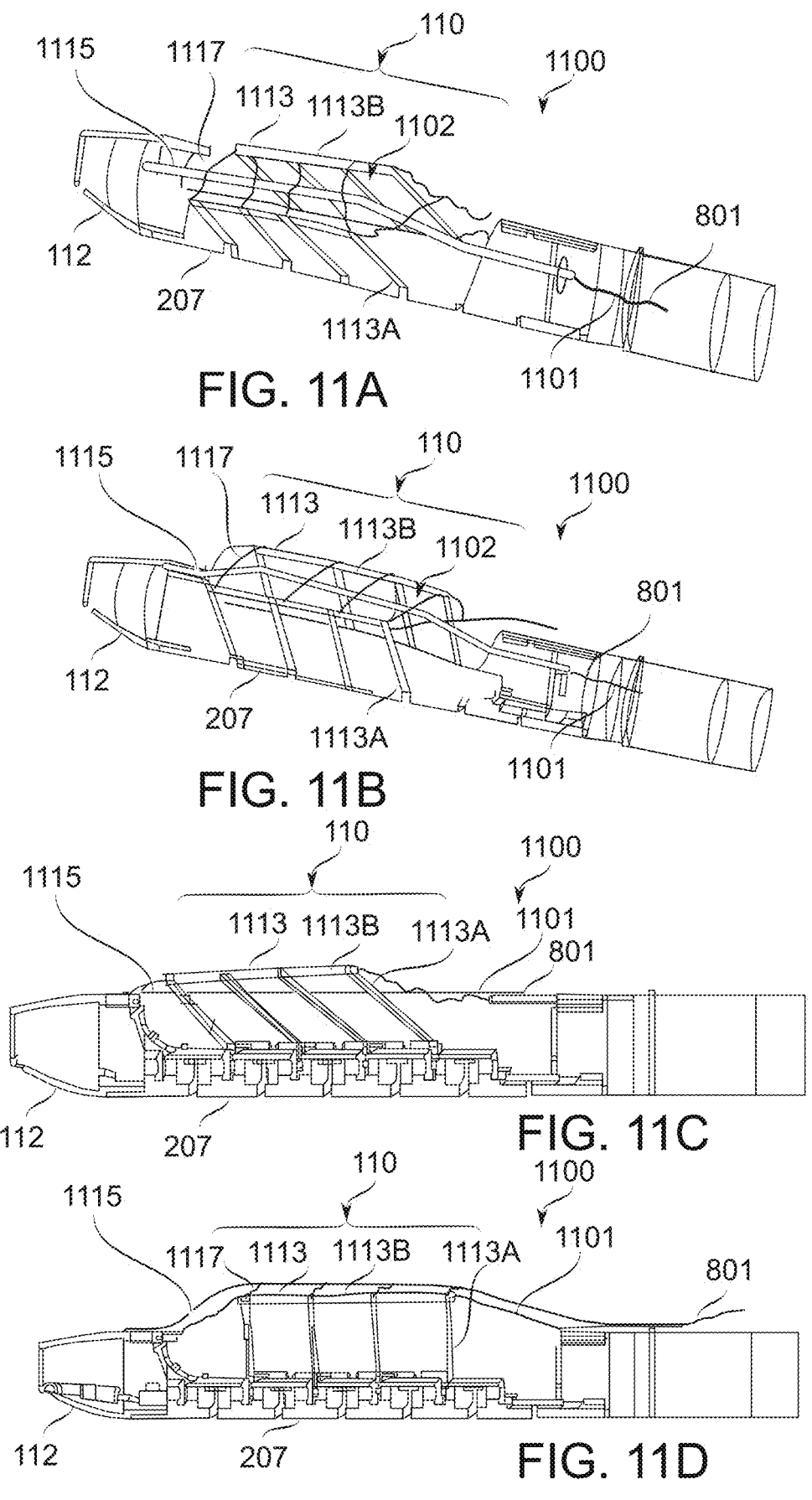

Reference is now made to FIGS. 10A-10D, which schematically represent a bougie capsule section 1000 comprising a capsule-expanding blocker 1015, along with a plurality of capsule-expanding flaps 1013, according to some embodiments of the present disclosure. Bougie capsule section 1000 is an example of a bougie capsule section 101. FIGS. 10A and 10D show perspective views of bougie capsule section 1000. FIGS. 10B and 10D show cross sectional views of bougie capsule section 1000, at the level of a pair of the flaps 1013. There may be provided, for example, 2, 4, 6, 8, 10, 12, or another number of flaps 1013.

In some embodiments, a capsule-expanding blocker 1015 and capsule expanding flaps 1013 are configured to move to expand a size of suction clamping domain 110 and a tissue-receiving space 1020 therein; for example, to open fenestrations 1002 of the aperture domain 110 to a larger size. As shown, fenestrations 1002 are bounded on two sides by lateral blockers 1017 (examples of lateral blockers 117), on one side by capsule-expanding blocker 1015, and on another side by flap edge 1013B.

The expansion has the potential advantage of increasing the amount and/or depth of lumen wall tissue that is held (potentially more securely) under vacuum. For example, by expanding each fenestration 1002, a greater depth of tissue can potentially be taken in by suction at the positions where needle penetration (e.g., by a helical needle 201) will occur during suturing.

Expansion of aperture domain 110 by movement of blocker 1015, in some embodiments, is substantially as described for blocker 815 of FIGS. 8A-9B (e.g., by operation of control member 801). In some embodiments, movement of blocker 1015 away from flaps 1013 allows tension in spring 1014 to cause flaps 1013 to open. Flaps 1013 may stop opening upon a stopping region 1016 contacting another part of the aperture domain 110 (e.g., spine region 1031).

Additionally, in the example of FIGS. 10A-10B, flaps 1013 are expandable, for example, by operation of (e.g., pulling) of control member 1001. Control member 1001 is an example of a control member 120.

In some embodiments, operation of control member 1001 causes flaps 1013 to swing (e.g., on a hinge) from a collapsed position to an expanded position. In some embodiments, the collapsed position comprises being arranged to point toward a midline plane that divides the aperture domain 110 along a dorsal/ventral plane of the aperture domain 110. In some embodiments, the expanded position comprises being arranged to point away from that midline plane. Optionally, each segment 207 is provided with a pair of flaps supports 1013. Optionally, flaps 1013 are provided just at the ends of the aperture domain, at the ends and in the middle of the aperture domain, or in another configuration.

Lateral blockers 1017 optionally comprise cords sized so that they become taut when aperture domain 110 is fully expanded. In some embodiments, the lateral blockers 117 are adjustable in tension to accommodate different degrees of expansion of longitudinal blocker 1015. In some embodiments, a control member 120 (not shown) is provided that can be manipulated to tighten/loosen slack in lateral blockers 1017.

In the example shown, FIGS. 10A and 10B show the flaps 1013 in fully collapsed positions. FIG. 10D shows flaps partially expanded, and FIG. 10C shows flaps 1013 fully expanded.

In some embodiments, the expanded aperture domain 110 is placed under vacuum to cause attachment to tissue.

As shown in FIG. 10C, fenestrations 1002 are oriented substantially perpendicular to a plane passing in a ventral-to-dorsal direction through aperture domain 110. To attach to tissue walls, the device is optionally first oriented that the fenestrations are substantially orthogonal to the tissue walls (e.g., gastric walls) which are to be attached to the device; one wall on either side. Upon application of suction, the collapsing tissue walls fold over flap edges 1013B onto the fenestrations 1002 and are secured. The two opposite tissue walls preferably meet at about the position of longitudinal blocker 1015. Optionally, the device is rocked during application of vacuum by slight rotations around its longitudinal axis, to help encourage filling of each fenestration 1102 by tissue from just one of the tissue walls.

Optionally, fenestrations 1002 expand to a more lateral-facing orientation than is shown in FIG. 10C. For example, capsule expanding blocker 1015 expands to a greater distance from a dorsal side of aperture domain 110, flaps 1013 are shorter, and/or flaps 1013 are oriented upon expansion so that flap edges 1013B lay closer to a dorsal side of aperture domain 110 than expanded capsule expanding blocker 1015, when flaps 1013 is expanded.

Reference is now made to FIGS. 11A-11D, which schematically represent a bougie capsule section 1100 comprising a capsule-expanding blocker 1115, along with a plurality of capsule-expanding outriggers 1113, according to some embodiments of the present disclosure.

FIGS. 11A-11D illustrate a different structure for expanding aperture domain 110, comprising supports 1113A which swivel from a flattened or relatively flattened position (e.g., as shown FIG. 11A) to a raised position having a position more perpendicular (FIGS. 11B, 11C) or perpendicular (FIG. 11D) to a longitudinal axis (along a distal-proximal direction) of bougie capsule section 1100.

Supports 1113A along each side, in some embodiments, are coupled to each other by stabilizing bars 1113B, which rise or fall as supports 1113A swivel around a swivel point attached to the capsule body. Actuation to change the expansion state of outriggers 1113, in some embodiments, comprises operation of a control member 1101. In some embodiments, capsule-expanding blocker 1115 is expanded (e.g., via control member 801), and optionally this expansion also induces expansion of outriggers 1113; e.g., by tension placed on lateral blockers 1117.

Fenestrations 1102 are defined, in some embodiments, as spaces bordered on two sides (e.g., the longitudinal axis borders) by lateral blockers 1117, on a medial side by capsule-expanding blocker 1115, and on a laterally outward side by a stabilizing bar 1113B.

Distal tip 112 and segments 207 are configured, for example, as described in relation to other figures herein.

Reference is now made to FIGS. 12A-12B, which schematically represent a bougie capsule section 1200 comprising a capsule-expanding blocker 1215, along with a plurality of capsule-expanding outriggers 1213, according to some embodiments of the present disclosure.

Actuation to change the expansion state of outriggers 1213, in some embodiments, comprises operation of a control member 1201.

FIGS. 12A-12B illustrate a different structure for expanding aperture domain 110 (i.e., a variation of the capsule-expanding outriggers 1013 described in relation to FIGS. 10A-10D), comprising crossed supports 1213A which swivel from a flattened or relatively flattened position (e.g., as shown in FIG. 12A) to a raised position (FIG. 12B).

In some embodiments, some of supports 1213A along each side are oriented to point in a more distal direction, and some in a more proximal direction, forming lattices, with separate supports 1213A formed as pieces coupled to each other via their crossings.

Alternatively, in some embodiments, lattice of supports 1213A is formed from a piece of shape-memory metal such as nitinol; for example, a piece which is normally collapsed (as in the configuration of FIG. 12A), but which deforms into an expanded shape, e.g., upon longitudinal compression (that is, compression along a distal-proximal axis of bougie capsule section 1200), and/or upon dorsal-ventral stretching (e.g., stretching induced through lateral blockers 117 upon expanding capsule-expanding blocker 1115 (e.g., via control member 801).

Fenestrations 1202 are defined, in some embodiments, as spaces bordered on two sides (e.g., the longitudinal axis borders) by lateral blockers 1217, on a medial side by capsule-expanding blocker 1215, and on a laterally outward side by portions of outriggers 1213.

Distal tip 112 and segments 207 are configured, for example, as described in relation to other figures herein.

Reference is now made to FIG. 20, which is a flowchart of a method of intralumenal use of a bougie capsule section, according to some embodiments of the present disclosure.

The flowchart begins, and at block 2200, in some embodiments, a suction clamping domain 200B of a bougie capsule section 200 is inserted to a body lumen (such as a stomach).

At block 2202, in some embodiments, a suturing space of the bougie capsule section, along the suction clamping domain, is expanded. In some embodiments, the expansion comprises use of a control member 120 to actuate movement of supports, for example, outriggers such as outriggers 1013, 1113, 1213. Additionally or alternatively, in some embodiments, the expansion comprises use of a control member to change the shape of a longitudinal blocker 115 extending longitudinally along the suction clamping domain. In some embodiments, the outriggers 1013, 1113, 1213 and/or longitudinal blocker 115 are also provided with lateral blockers 117. Together, these structures, upon expansion, define supporting surfaces onto which tissue collapses upon application of suction (in block 2204), and define fenestrations 111 through which the collapsing tissue enters into a suturing space located along the suction clamping domain.

At block 2204, in some embodiments, suction is applied. Under the force of suction, body lumen tissue collapses onto the expanded supporting surfaces of the suction clamping domain 200B. Some of the body lumen tissue is sucked into the suturing space defined at the level of suction clamping domain 200B by apertures between the supporting surfaces; for example, sucked into the suturing space through fenestrations. In some embodiments, the collapsed tissue is arranged so that tissue from one portion of a body lumen wall is sucked into a left lateral set of fenestrations, and tissue from another (e.g., facing) portion of a body lumen wall is sucked into a right lateral set of fenestrations. Optionally, the midline between right and left is defined by the longitudinal blocker 115.

Optionally, in some embodiments, the method of FIG. 20 continues with block 2206, in which a helical needle 201 is longitudinally advanced by rotation along the expanded portion of the suturing space. In some embodiments, helical needle 201 is longitudinally advanced by frictional contacts with a rotating shaft 205, wherein the frictional contacts occur at positions along the bent portion of the suturing space.

Vacuum Distribution

Reference is now made to FIGS. 13A-13D, which schematically represent internal structures of a bougie suction clamping domain 200B affecting vacuum distribution, tissue clogging, and/or tissue clamping, according to some embodiments of the present disclosure. FIG. 13A shows bougie suction clamping domain 200B from a ventral side looking dorsally. FIG. 13B shows bougie suction clamping domain 200B from a perspective view. FIGS. 13C-13D show side-views of bougie suction clamping domain 200B. FIG. 13C shows a side-view from proximal end 1320 of suction clamping domain 200B, and FIG. 13D shows a side-view from distal end 1321 of suction clamping domain 200B.

In some embodiments, features of bougie aperture domain 200B include housings 310, gaps 311A, needle channels 311, cavity 208, segments 207, and apertures 206, for example as described in relation to FIGS. 2A-2B, herein.

In some embodiments, segments 207 include inward-protruding portions 1300 defined between needle channels 311, and protruding into an interior area (tissue receiving space 1330) of suction clamping domain 200B from a dorsal side 1303 of suction clamping domain 200B. Inward-protruding portions 1300, in some embodiments, comprise laterally projecting branches 1305, defining spaces 1302 between branches 1305 and dorsal side 1303, to which tissue access (upon application of suction) is restricted by a relatively narrow slot 1302B. For example, slot 1302B is about 2-3 mm across. Potentially, the narrowness of slot 1302B helps ensure that spaces 1302 remain at least partially open when suction is applied, which in turn assists in ensuring that low pressure due to applied suction is distributed uninterruptedly along bougie aperture domain 200B. In some embodiments, applied suction bends tissue so that it contacts branches 1305 from both within space 1302, and outside of space 1302, e.g., along a ventrally-facing surface 1307 which is within a tissue-receiving space defined by suction clamping domain 200B.

In some embodiments, the convolution of tissue around inward-protruding portion 1300 as it deforms under vacuum to fill into the shape of spaces 1302 acts to help hold tissue in place during suturing. Potentially, this helps to keep tissue from being "bunched up" by movement of the needle, and/or to help reduce a risk of tissue tearing as the needle is advanced through the tis sue.

Optionally, surface 1307 is shaped with a curvature and placed at an inset from the inner dorsal side of suction clamping domain 200B so that an endoscope (e.g., of up to about 6-8 mm in diameter) can be passed through the tissue-receiving space 1330 of suction clamping domain 200B.

In some embodiments, inward-protruding portion 1300 is hollowed on a ventrally-facing surface. This potentially acts to help receive a sufficient thickness of tissue upon activation of suction.

Aperture 1301, in some embodiments, is sized for the admittance of shaft 205 and/or pin 205B, for example as these elements are described in relation to FIGS. 2A-2B.

Offset Fenestrations

Reference is now made to FIGS. 14A-14B, which schematically represent a suction clamping domain 200B of a bougie capsule section 1401 comprising offset fenestrations defined by tissue supports 1403A, 1405B, according to some embodiments of the present disclosure. Reference is also made to FIGS. 15A-15C, which schematically represent variations of suction clamping domain 200B of a bougie capsule sections 1501, 1522, 1543 comprising offset fenestrations defined by tissue supports 1503A, 1503B, 1523C, 1523B, 1523D, 1523E, according to some embodiments of the present disclosure.

Tissue supports 1403A, 1405B, 1503A, 1503B, 1523C, 1523B, 1523D, 1523E, in some embodiments, are distributed in alternation along two sides of a longitudinal midline of bougie capsule section 1401. The tissue supports can be of different longitudinal lengths along one side of the midline, and/or of different longitudinal lengths along different sides of the midline.

In use, when suction clamping domain 200B is engaged with tissue walls under suction inside a body cavity, a suturing needle (for example, suturing needle 201 of FIGS. 2A-2B) is spirally advanced along suction clamping domain 200B. Needle 201 alternately penetrates tissue intrusions on either side of the midline.

In some embodiments, a longitudinal blocker (not shown, but received, for example, by anchoring cavity 208 of FIGS. 14A-14B, 15C) is provided to help define and maintain boundaries between fenestrations 1402. The extent of medial protrusion of tissue supports 1403A, 1405B, 1523D, 1523C may be restricted, for example, and the space left partially filled in by a longitudinal blocker such as longitudinal blocker 115.

Optionally, no longitudinal blocker is used, and the shapes of tissue supports 1503A, 1503B, 1523C, 1523B are sized and spaced to ensure separation of tissue on alternate sides.

Suture may be disengaged by passing out in the gaps 1407 between adjacent corners of tissue supports 1403A, 1405B.

Progressive Fenestrations

Figure 17E:
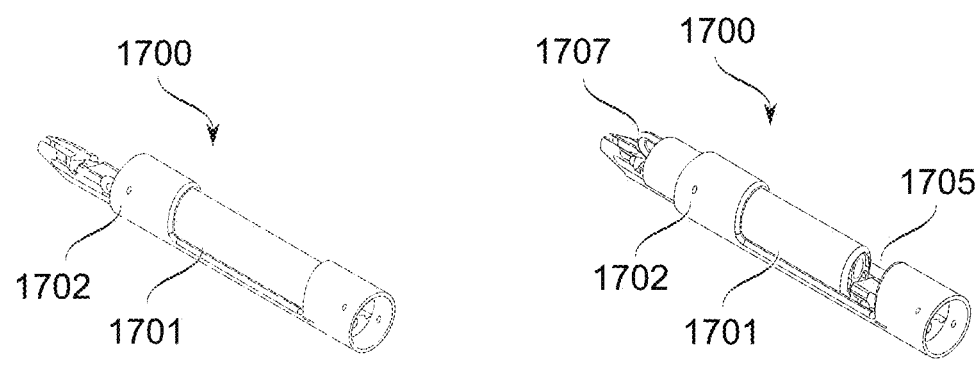
Figure 17E:
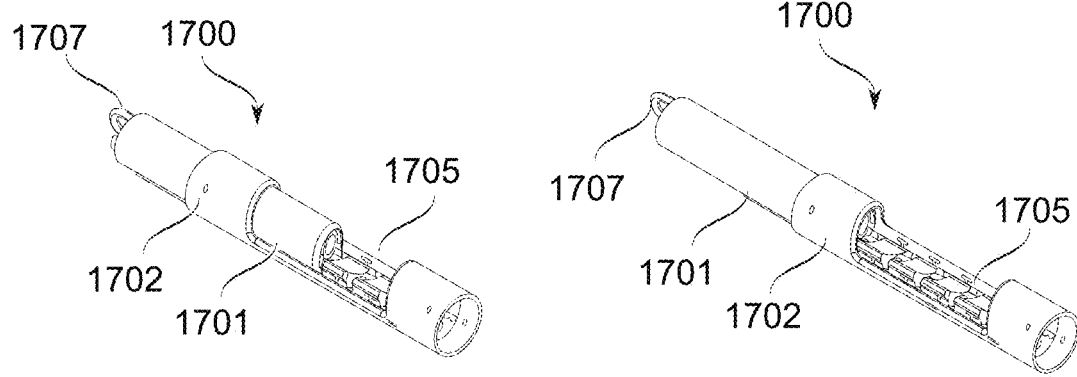
Figure 17E:
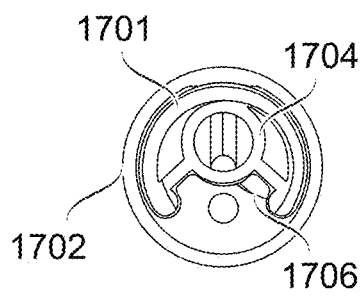

Reference is now made to FIGS. 16A-16B, which schematically represent an arrangement of a suction clamping domain 1605 allowing progressive unblocking of a fenestration 1603 by longitudinal blocker 1601, according to some embodiments of the present disclosure. Reference is also made to FIGS. 17A-17E, which schematically represent an alternative arrangement of a suction clamping domain 1700 allowing progressive unblocking of a fenestration 1705 by a longitudinal blocker 1701, according to some embodiments of the present disclosure. FIGS. 17A-17D represent different stages of withdrawal of longitudinal blocker 1701. FIG. 17E represents a cross-section at a level of longitudinal blocker 1701, according to some embodiments of the present disclosure. Further reference is made to FIGS. 18A-18B, which schematically represent an alternative arrangement of a suction clamping domain 1800 allowing progressive unblocking of a fenestration 1802 by longitudinal blocker 1801, according to some embodiments of the present disclosure. FIGS. 18A-18B represent different stages of withdrawal of longitudinal blocker 1801.

In some embodiments, a portion of a bougie body 1600, 1702, 1806 defines a large fenestration 1603, 1705, 1802 (optionally a single large fenestration) which is gradually lengthened along a longitudinal axis of the bougie body by longitudinal movement (e.g., by withdrawal proximally) of longitudinal blocker 1601, 1701, 1801 e.g., actuated by control member 1602, 1707, 1821. In some embodiments, the large fenestration 1603, 1705, 1802 has a length along the longitudinal axis of, for example, at least 4 cm, 5 cm, 6 cm, 10 cm, or 15 cm. The length, in some embodiments, is long enough to allow placement of at least 2, 3, 4, 5 or more sutures, for example by proximally advancing spiral needle 201. After positioning within a body cavity: as the longitudinal blocker 1601, 1701, 1801 is withdrawn to reveal more of fenestration 1603, 1705, 1802; more tissue is suctioned inside, and made available for suturing, for example by a proximally advancing spiral needle 201.

In some embodiments (FIGS. 16A-16B, 18A-18B), longitudinal blocker 1601, 1801 comprises a wide portion 1601A, 1803 and a narrow portion 1601B, 1805. Narrow portion 1601B, 1805 helps to define two laterally separated sides of fenestration 1603, 1802, so that tissue—from, for example, opposite body cavity walls—is guided into one side or the other of fenestration 1603, 1802, without one body cavity wall side completely filling the available space.

Optionally, (FIGS. 18A-18B), longitudinal blocker 1801 also comprises a divider 1807 which intrudes into the internal space defined by bougie body 1806, and acts to also block internally intruding tissue under suction so that it is prevented from crossing a midline of bougie body 1806.

In FIG. 17E, a portion of the internal structure of a longitudinal blocker 1701 is shown, comprising internal supporting struts 1704 (curved and/or straight). Optionally, longitudinal blocker 1701 is shaped so that it is locked to shape of body 1702, for example, using inward protruding portion 1706 as a guide rail.

In some embodiments, wide portion 1803 is slit along its lengths by slits 1810. This potentially helps to maintain flexibility of bougie body 1806, and/or to assist in the vacuum collapse under suction of body tissue walls of a body cavity to which bougie body 1802 is inserted.

General

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the present disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments may be presented with reference to a range format. It should be understood that the description in range format is merely for convenience and brevity and should not be construed as an inflexible limitation on the scope of descriptions of the present disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although descriptions of the present disclosure are provided in conjunction with specific embodiments, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

It is appreciated that certain features which are, for clarity, described in the present disclosure in the context of separate embodiments, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

In addition, any priority document(s) of this application is/are hereby incorporated herein by reference in its/their entirety.

What is claimed is:

1. A bougie capsule section configured for shaping and suturing of tissue of a body lumen from within the body lumen, the bougie capsule section comprising:
    a capsule body, extending longitudinally between a distal side and a proximal side of the bougie capsule section, said capsule body having a longitudinal axis;
    an arcuate needle within the capsule body comprises a relatively high-friction surface; and
    a shaft, extending longitudinally along the capsule body, said shaft positioned radially within an arc of said arcuate needle, said shaft positioned relative to said capsule body such that said shaft is offset from said capsule body longitudinal axis, said shaft frictionally coupled to said arcuate needle and rotatable to rotatably drive rotation of the arcuate needle around the longitudinal axis of the capsule body, wherein the driving is by friction between a body of the shaft and the arcuate needle at a plurality of spaced apart locations along said arcuate needle.

2. The bougie capsule section of claim 1, wherein the arcuate needle is a helical needle, and the rotation of the helical needle is accompanied by translation of the helical needle along the longitudinal axis of the capsule body.

3. The bougie capsule section of claim 2, wherein the capsule body defines a helical arrangement of channels along which the helical needle rotates and advances longitudinally; and the shaft presses against the helical needle in at least one position where the shaft crosses the helical arrangement of channels.

4. The bougie capsule section of claim 1, wherein the shaft is radially within an arc of the arcuate needle where the shaft presses against the arcuate needle.

5. The bougie capsule section of claim 1, wherein the capsule body and shaft are flexible along a region where the shaft presses against the arcuate needle.

6. The bougie capsule section of claim 1, wherein the arcuate needle comprises a relatively low-friction surface.

7. The bougie capsule section of claim 6, wherein the low-friction surface of said arcuate needle presses outwardly against the surfaces of the capsule body.

8. The bougie capsule section of claim 1, wherein the shaft comprises a cable section comprising a plurality of strands, and a pin section comprising a solid piece, positioned along the capsule body where the pin section presses against the arcuate needle.

9. The bougie capsule section of claim 8, wherein the pin section has a fixed and uniform diameter.

10. The bougie capsule section of claim 8, wherein the pin section is tapered.

11. The bougie capsule section of claim 8, wherein the shaft is configured to move longitudinally as it rotates.

12. The bougie capsule section of claim 11, wherein longitudinal movement of the pin section maintains contact of the pin section with the needle during a longitudinal movement of the needle.

13. The bougie capsule section of claim 1, wherein the capsule body comprises a plurality of longitudinally aligned lumens arranged along the capsule body, and through which the shaft passes; wherein the shaft is held against the arcuate needle at one or more positions between the longitudinally aligned lumens.

14. The bougie capsule section of claim 1, wherein the capsule body defines a suction clamping domain defined by supporting surfaces positioned along the suction clamping domain, configured to receive the tissue of the body lumen collapsed onto the supporting surfaces upon application of suction to the suction clamping domain while the bougie capsule section is inserted in the body lumen.

15. The bougie capsule section of claim 14, comprising:

a suturing space defined by supporting surfaces of the suction clamping domain, configured to receive the tissue of the body lumen collapsed onto the supporting surfaces upon application of suction to the suction clamping domain while the bougie capsule section is inserted in the body lumen;

wherein the capsule body comprises articulated segments, configured to change angle with respect to each other to produce a bend in the capsule body.

16. The bougie capsule section of claim 15, wherein the suction clamping domain comprises the articulated segments.

17. The bougie capsule section of claim 15, wherein the articulated segments are longitudinally interconnected in a single continuous piece, and the articulation between segments comprises thinning of material of the single continuous piece to form articulation joints.

18. The bougie capsule section of claim 15, wherein the articulated segments define helically arranged channels, and comprising a helical needle, configured to advance longitudinally as it rotates through the helically arranged channels, while the articulated segments are bent.

19. The bougie capsule section of claim 15, wherein the bend is produced by operation of a control member attached to the capsule body via a longitudinal blocker that extends longitudinally through the suction clamping domain to provide a portion of the supporting surfaces, and longitudinally divides an aperture region into separate fenestrations on either side of the longitudinal blocker, said fenestrations leading into a suturing space; and wherein movement of the longitudinal blocker upon the longitudinal movement of the control member produces the bend in the capsule body.

20. The bougie capsule section of claim 15 wherein the bougie capsule section is expandable by movement of the supporting surfaces.

21. The bougie capsule section of claim 20, wherein expansion of the bougie capsule section increases a cross-sectional size of the suturing space by outward movement of the supporting surfaces.

22. The bougie capsule of claim 1, wherein said shaft comprises a relatively high-friction surface region.

23. The bougie capsule of claim 2, wherein said relatively high-friction surface includes a high friction coating.

24. The bougie capsule of claim 1, wherein said arcuate needle is pressed between said shaft and surfaces of the capsule body.

25. The bougie capsule of claim 1, wherein said shaft is frictionally coupled to said arcuate needle and rotatable to drive, by friction between the body of the shaft and the arcuate needle, wherein said body of said shaft presses against said needle in a direction which is radially outward relative to said capsule body, and wherein rotation of the arcuate needle is around the longitudinal axis of the capsule body.

26. A bougie capsule section configured for shaping and suturing of tissue of a body lumen from within the body lumen, the bougie capsule section comprising:

a capsule body, extending longitudinally between a distal side and a proximal side of the bougie capsule section, said capsule body having a longitudinal axis;

an arcuate needle within the capsule body comprises a relatively high-friction surface, wherein said arcuate needle has a longitudinal axis that is offset from said capsule body longitudinal axis; and a shaft, extending longitudinally along the capsule body, said shaft positioned radially within an arc of said arcuate needle, said shaft positioned relative to said capsule body such that said shaft is offset from said capsule body longitudinal axis, said shaft frictionally coupled to said arcuate needle and rotatable to drive rotation of the arcuate needle around the longitudinal axis of the capsule body, wherein the driving is by friction between the shaft and the arcuate needle.

27. A method of intraluminal suturing, comprising:

rotating a helical needle having a relatively high-friction surface and a relatively low-friction surface by frictional interaction with a rotating shaft pressing against the high-friction surface to advance the helical needle along a bougie capsule section, wherein the rotating shaft is positioned radially within an arc of the helical needle, wherein said bougie capsule section has a longitudinal axis, and wherein the shaft is offset from the bougie capsule section longitudinal axis, a body of the shaft frictionally coupled to the helical needle at a plurality of spaced apart locations along the helical needle.

28. The method of claim 27, wherein the shaft is fitted longitudinally along the bougie capsule section to press against the helical needle.

29. The method of intraluminal suturing of claim 27, comprising:

inserting to a body lumen a suction clamping domain of said bougie capsule section configured for shaping and suturing of tissue of a body lumen from within the body lumen;

inducing a bend along the suction clamping domain;

applying suction to collapse tissue of the body lumen onto supporting surfaces of the suction clamping domain, and into a suturing space within the bent bougie capsule section; and wherein said rotating comprises advancing said helical needle through the suturing space and through the bend by said rotating of the helical needle.

* * * * *